US007282623B2

(12) United States Patent
Thomas

(10) Patent No.: US 7,282,623 B2
(45) Date of Patent: Oct. 16, 2007

(54) PRODUCTION OF GAMMA LINOLENIC ACID BY A Δ 6-DESATURASE

(75) Inventor: Terry L. Thomas, College Station, TX (US)

(73) Assignee: Rhone-Poulenc Agrochimie, Lyons Cedex (FR)

( * ) Notice: Subject to any disclaimer, the term of this patent is extended or adjusted under 35 U.S.C. 154(b) by 525 days.

(21) Appl. No.: 10/702,777

(22) Filed: Nov. 6, 2003

(65) Prior Publication Data

US 2004/0078845 A1    Apr. 22, 2004

Related U.S. Application Data

(60) Division of application No. 09/685,775, filed on Oct. 10, 2000, now Pat. No. 6,683,232, which is a division of application No. 08/934,254, filed on Sep. 19, 1997, now Pat. No. 6,355,861, which is a continuation-in-part of application No. 08/789,936, filed on Jan. 28, 1997, now Pat. No. 5,789,220, which is a continuation-in-part of application No. 08/307,382, filed on Sep. 14, 1994, now Pat. No. 5,552,306, which is a continuation of application No. 07/959,952, filed on Oct. 13, 1992, now abandoned, which is a continuation-in-part of application No. 07/817,919, filed on Jan. 8, 1992, now abandoned, which is a continuation-in-part of application No. 07/774,475, filed on Oct. 10, 1991, now abandoned.

(51) Int. Cl.
*A01H 5/00* (2006.01)
*C12N 15/82* (2006.01)

(52) U.S. Cl. ...................... 800/281; 435/468
(58) Field of Classification Search ............ None
See application file for complete search history.

(56) References Cited

U.S. PATENT DOCUMENTS 4,736,866 A    4/1988    Leder et al. .................. 800/1

FOREIGN PATENT DOCUMENTS

| EP | A0255378 | 2/1988 |
| GB | WO99/27111 | 6/1999 |
| WO | WO9010076 | 9/1990 |
| WO | WO94/18337 | 8/1994 |

OTHER PUBLICATIONS

Aebersold, et al. (1987) "Internal amino acid sequence analysis of proteins separated by one or two-dimensional gel electrophoresis after in situ protease digestion on nitrocellulose", *Proc. Natl. Acad. Sci. USA 84*: 6970-6974.
Bafor, et al. (1990) "Properties of the Glycerol Acylating Enzymes in Microsomal Preparations from the Developing Seeds of Safflower(*Carthamus tinctorius*) and Turnip Rape (*Brassica campestris*) and their Ability to Assemble Cocoa-Butter Type Fats", *Journal of the American Oil Chemists Society 67*: 217-225.

Brenner (1976) "Regulatory Function of Δ6-Desaturase—A Key Enzyme of Poly-unsaturated Fatty Acid Synthesis", *Adv. Exp. Med. Biol. 83*: 85-101.
Crozier, et al. (1989) "Black Currant Seed Oil Feeding and Fatty Acid in Liver Lipid Classes of Guinea Pigs", *Lipids 24*: 460-466.
Dahmer, et al. (1989) "A Rapid Screening Technique for Determining the Lipid Composition of Soybean Seed", *J. Amer. Oil Chem. Soc. 66*: 543-548.
Devereux, et al. (1984) "A Comprehensive Set of Sequence Analysis programs for the VAX", *Nucleic Acids Res. 12*: 387-395.
Golecki, et al. (1982) "The Biology of the Cyanobacteria", (Eds. Carr and Whitton), pp. 125-141.
Harpester, et al. (1988) "Relative strengths of the 35S cauliflower mosaic virus, 1', 2', and nopaline synthase promoters in transformed tobacco sugarbeet and oilseed rape callus tissue", *Mol. Gen. Genet 212*: 182-190.
Horrobin, et al. (1984) "Effects of Essential Fatty Acids on Prostaglandin Biosynthesis", Biomed. Biochim. Acta 43: S114-S120.
Jaye, et al. (1983) "Isolation of a human anti-haemophilic factor IX cDNA clone using a unique 53-base synthetic oligonucleotide probe deduced from the amino acid sequence of bovine factor IX", *Nucleic Acids Research 11*(8): 2325-2335.
Kenyon, et al. (1972) "Fatty Acid Composition and Physiological Properties of Some Filamentous Blue-Green Algae", *Arch. Mikrobiol. 83*: 216-236.
Kenyon (1972) "Fatty Acid Composition of Unicellular Strains of Blue Green Algae", *J. Bacteriology 109*: 827-834.
Kyte, et al. (1982) "A Simple Method for Displaying the Hydropathic Character of a Protein", *J. Mol. Biol. 157*: 105-132.
Miguel, et al. (1992) "Arabidopsis Mutants Deficient in Polyunsaturated Fatty Acid Synthesis", *J. Biol. Chem. 267*: 1502-1509.
Murata, et al. (1987) "Lipids of Blue Green Algae (Cyanobacteria)" In: Stumpf PK (eds) *The Biochemistry of Plants*, Academic Press, Orlando, FL. 9: 315-347.
Murata, et al. (1989) "Low-Temperature Effects on Cyanobacterial membranes", *Journal of Bioenergetics and Biomembranes 21*: 60-75.
Murphy, et al. (1989) "Are the promoter regions of seed storage protein genes suitable for the expression of genes involved in storage lipid synthesis?", *Biochem. Soc. Transactions 17*: 685-686.
Ohlrogge, et al. (1991) "The Genetics of Plant Lipids", *Biochim. Biophys. Acta. 1082*: 1-26.

(Continued)

Primary Examiner—Elizabeth F McElwain
(74) Attorney, Agent, or Firm—Scully, Scott, Murphy & Presser, P.C.

(57) ABSTRACT

Linoleic acid is converted into γ-linolenic acid by the enzyme Δ6-desaturase. The present invention is directed to isolated nucleic acids comprising the Δ6-desaturase gene. More particularly, the isolated nucleic acid comprises the promoter, coding region and termination regions of the Δ6-desaturase gene. The present invention provides recombinant constructions comprising the Δ6-desaturase coding region in functional combination with heterologous regulatory sequences. The nucleic acids and recombinant constructions of the instant invention are useful in the production of GLA in transgenic organisms.

21 Claims, 27 Drawing Sheets

OTHER PUBLICATIONS

Ow, et al. (1987) "Functional regions of the cauliflower mosaic virus 35S RNA promoter determined by use of the firefly luciferase gene as a reporter of promoter activity", *Proc. Natl. Acad. Sci. USA 84*: 4870-4874.

Ripka, et al. (1979) "Generic Assignments, Strain Histories and Properties of Pure Cultures of Cyanobacteria", *J. General Micro. 111*: 1-61.

Sanger, et al. (1977) "DNA Sequencing with Chain-Terminating Inhibitors", *Proc. Natl. Acad. Sci. USA 74*: 5463-5467.

Shanklin, et al. (1991) "Stearoyl-acyl-carrier-protein Desaturase from Higher Plants is Structurally Unrelated to the Animal and Fungal Homologs", *Proc. Natl. Acad. Sci., USA 88*: 2510-2514.

Somerville, et al. (1991) "Plants Lipids: Metabolism, Mutants, and Membranes", *Science 252*: 80-87.

Stumpf (1987) "Plant Lipid Biotechnology Through the Looking Glass", *J. American Oil Chemical Society 65*: 1641-1645.

Stymne, et al. (1986) "Biosynthesis of γ-Linolenic Acid in Cotyledons and Microsomal Preparations of the Developing Seeds of Common Borage (*Borago officinalis*)", *Biochem. J. 240*: 385-393.

Sugano, et al. (1986) "Effects of mold Oil Containing γ-Linolenic Acid on the Blood Cholesterol and Eicosanoid Levels in Rats", *Agric. Biol. Chem. 50*: 2483-2491.

Wada, et al. (1980) "Enhancement of Chilling Tolerance of a Cyanobacterium by Genetic Manipulation of Fatty Acid Desaturation", *Nature 374*: 200-203.

Weete, J.D. (1980) *Lipid Biochemistry of Fungi and Other Organisms*, Plenum Press, New York, Chapter 6, 157-163.

Yadav, et al. (1993) "Cloning of Higher Plant ω-3 Fatty Acid Desaturases", *Plant Physiology 103*: 467-476.

Galle, et. al. (1995) "Solubization of Δ12- and Δ6-Desaturases from Seeds of Borage Microsomes" in *Plant Lipid Metabolism; 11th International Meeting on Plant Lipids*, Paris, France, Jun. 26-Jul. 1, 1994, Kluwer Academic Publishers, Netherlands, pp. 509-511.

Griffiths, et al. (1988) "Δ6- and Δ12-Desaturase Activities and Phosphatidic Acid Formation in Microsomal Preparations from the Developing Cotyledons of Common Borage (*Borago officinalis*)" in *The Biochemical Journal 252*(3): 641-647.

Galle, et al. (1993) "Biosynthesis of γ-Linolenic Acid in Developing Seeds of Borage (*Borago officinalis L.*)", in *Biochimica et Biophysica Acat 1158*: 52-58.

Schmidt, et al. (1994) "Purification and PCR-Based cDNA Cloning of a Plastidial n-6 Desaturase" in *Plant Molecular Biology 26*: 631-642.

Bafor, et al. (1990) "Properties of Glycerol Acylating Enzymes in Microsomal Preparations from the Developing Seeds of Safflower (*Carthamus tinctorius*) and Turnip Rape (*Brassica campestris*) and their Ability to Assemble Cocoa-Butter Type Fats" in *JAOCS 67*: 217-225.

Kodama, et al. (1994) "Genetic Enhancement of Cold Tolerance by Expression of a Gene for Chloroplast ω-3 Fatty Acid Desaturase in Transgenic Tobacco" in Plant Physiol. 105: 601-605.

Broun et a., Science 282: 131-133, Nov. 13, 1998.

Van de Loo et al., Proc. Natl. Acad. Sci, USA, 92: 6743-6747, Jul. 1995.

Doerks et al., TIG 14(6): 248-250, Jun. 1998.

Smith, et al., Nature Biotechnology 15: 1222-1223, Nov. 1997.

Brenner, S.E., TIG 15(4): 132-133, Apr. 1999.

Bork, et al., TIG 12(10): 425-427, Oct. 1996.

De Luca, V. AgBIotech News and Information 5(6): 225N-229N, 1993.

1   MAAQIKKYIT  SDELKNHDKP  GDLWISIQGK  AYDVSDWVKD  HPGGSFPLKS
 81   LKDYSVSEVS  KDYRKLVFEF  SKMGLYDKKG  HIMFATLCFI  AMLFAMSVYG
161   AGHYMVVSDS  RLNKFMGIFA  ANCLSGISIG  WWKWNHNAHH  IACNSLEYDP
241   SLSRFFVSYQ  HWTFYPIMCA  ARLNMYVQSL  IMLLTKRNVS  YRAQELLGCL
321   GMQQVQFSLN  HFSSSVYVGK  PKGNNWFEKQ  TDGTLDISCP  PWMDWFHGGL
401   HNLPYNYASF  SKANEMTLRT  LRNTALQARD  ITKPLPKNLV  WEALHTHG
```

FIGURE 5B(1)

```
LAGQEVTDAF  VAFHPASTWK  NLDKFFTGYY   80
VLFCEGVLVH  LFSGCLMGFL  WIQSGWIGHD  160
DLQYIPFLVV  SSKFFGSLTS  HFYEKRLTFD  240
VFSIWYPLLV  SCLPNWGERI  MFVIASLSVT  320
QFQIEHHLFP  KMPRCNLRKI  SPYVIELCKK  400
                                    448
```

FIGURE 5B(2)

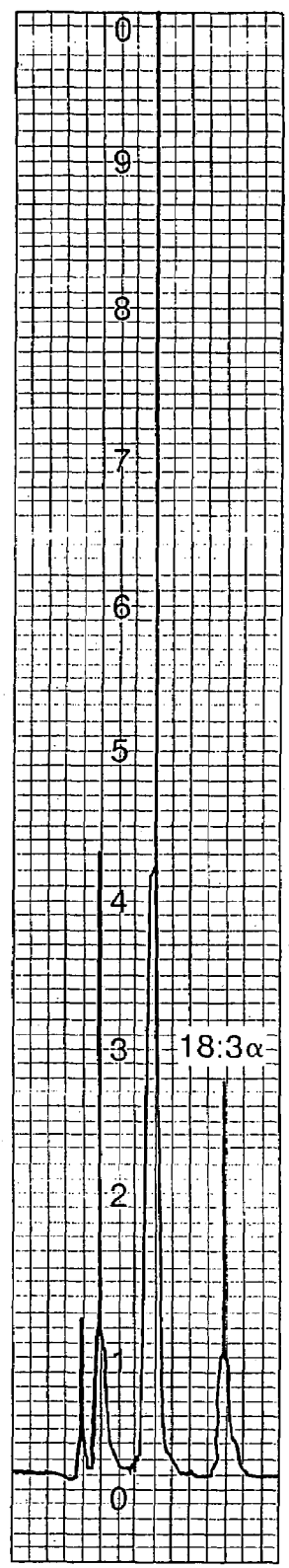
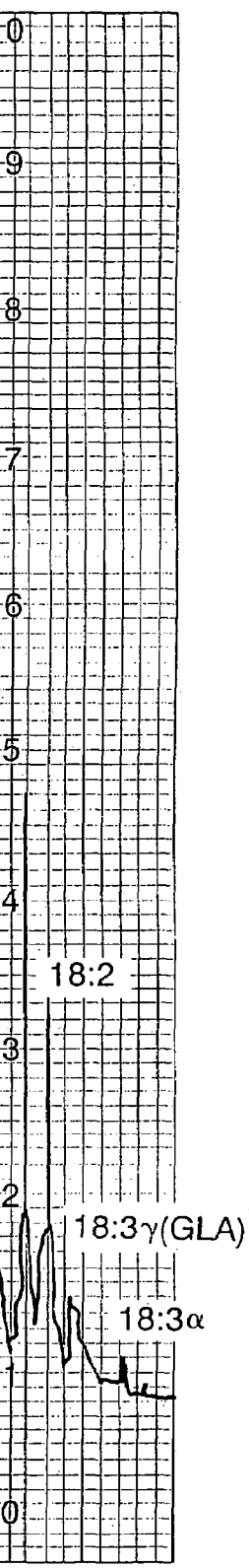
FIGURE 8A             FIGURE 8B

Complete DNA sequence and deduced amino acid sequence of
Evening Primrose Putative Δ6-desaturase

```
CCCCAAAAAATTTCATTGTTCTCCATCTGGACCACAGCA
GCT AAG AAG TAT ATC ACG GCG GAG GAC CTC CGC CGC CAC AAC
 A   K   K   Y   I   T   A   E   D   L   R   R   H   N
ATC TCC ATC CAG GGC AAG GTC TAC GAC GTC GAC TCT CGG TGG GCG
 I   S   I   Q   G   K   V   Y   D   V   D   S   R   W   A
GAG GTC CCG CTC ATG CTG CAT ATG CGG GGC GCC CAG CCG GAT GGC GAC
 E   V   P   L   M   L   H   M   R   G   A   Q   P   D   G   D
CCG GGC ACG GCG TGG CGG ATC TCC AAG TAC GAC CTG TAC CGG ACC ACC
 P   G   T   A   W   R   I   S   K   Y   D   L   Y   R   T   T
GAA TCG GAG AAG AAG GGC GGG CAC CAC CAC CAC ATG TGG AGG TGG CTT ACG TTC GTC
 E   S   E   K   K   G   G   H   H   H   H   M   W   R   W   L   T   F   V
ATC TTC AtC GTC GTC TAC GGG CTG CTG CTG CTG TCG GAG TCC TAT TTC GTC
 I   F   I   V   V   Y   G   L   L   L   L   S   E   S   Y   F   V
GCG GCA GCA GCA GCA GCC GCC ATC GCC CAA GCC GCG GCG GCG GCG GCG
 A   A   A   A   A   A   I   A   Q   A   A   A   A   A   A
GCA CTG CTG GGC GGC GGC GGC GGC GGC
 A   L   L   G   G   G   G   G   G
```

FIGURE 10A

TCCACACAATG GAG GGC GAA
          M   E   G   E
AAG TCC GGC GAT CTC TGG
 K   S   G   D   L   W
GCG GAG CAC CCC GGC GGC
 A   E   H   P   G   G
GCC TTC ATT GCG TAC CAC
 A   F   I   A   Y   H
TAC TAC CTC AAG GAC TTC
 Y   Y   L   K   D   F
GAG ATG TCG CGG TCC GGG
 E   M   S   R   S   G
GGC GTT GCG GTC CTC ATG
 G   V   A   V   L   M
GTT CAC ATG CTC TGC GGC
 V   H   M   L   C   G
CAT GAC TCC GGC CAT TAC
 H   D   S   G   H   Y

FIGURE 10B

```
CAG GTG ATG CCA ACC CGT GGA TAC AAC AGA ATC ACG CAA CTC
 Q   V   M   P   T   R   G   Y   N   R   I   T   Q   L
ACC GGA ATC AGC ATC GCG CCC TGG TAC AAG TGG CAC AAC GCC
 T   G   I   S   I   A   P   W   Y   K   W   H   N   A
AGC CTC GAC TAC GAC ATC GAC CTC TTC CAG CTC TTC CAC CCC TTC GTA TTC
 S   L   D   Y   D   I   D   L   F   Q   L   F   H   P   F   V   F
TTC AAC TCC ACC TAC ACC TCG CAG GAC GTC TTC TTA CAC GCA CAT GGC CGA GTC CTG AAA
 F   N   S   T   Y   T   S   Q   D   V   F   L   H   A   H   G   R   V   L   K
TTC CTA TTC TAC ACC ATC TTT GCG TTA GTT TGG CTC TGG TAC CCG ATG
 F   L   F   Y   T   I   F   A   L   V   W   L   W   Y   P   M
CTC TTC ATG CAG GGT ATC CGG TTC GGG ACG CTC ACG CTC CCG GTC GAC
 L   F   M   Q   G   I   R   F   G   T   L   T   L   P   V   D
AAC TTA CCT GAA GGT CAC CAC TTC TTC TTC AGG CCG CTC ATG GAC
 N   L   P   E   G   H   H   F   F   F   R   P   L   M   D
AAC TGG ACG CTC AAC CAC TGG ATC AGC TCC ATC GCG
 N   W   T   L   N   H   W   I   S   S   I   A
GTC CAG TTC ACA GAC ACA GAC TAC GTG
 V   Q   F   T   D   T   D   Y   V
```

FIGURE 10C

```
ATA GCA GGC AAC ATC CTA
 I   A   G   N   I   L
CAC CAC CTC GCC TGC AAC
 H   H   L   A   C   N
GCC GTC TCC ACC GGA CTC
 A   V   S   T   G   L
TTC GAC GAA GTG CGA CGG
 F   D   E   V   R   R
ATC TTC GGC GCA GCT AAC
 I   F   G   A   A   N
GTC CCT GAC CGC GTC CTA
 V   P   D   R   V   L
TTC GTA TCT TGT ATC CCG
 F   V   S   C   I   P
GTC ACG GCG GCC CAG CAC
 V   T   A   A   Q   H
GGC CCC CCC AAG GGC GAC
 G   P   P   K   G   D
```

FIGURE 10D

```
AAC TGG TTC GAG AAG CAG ACG AAA GGG ACG ATC GAT ATC ACG
 N   W   F   E   K   Q   T   K   G   T   I   D   I   T
TGG TTC TTT GGT GGG CTG CAG TTC CAG TTG GAG CAC CAC TTG
 W   F   F   G   G   L   Q   F   Q   L   E   H   H   L
GGG CAG CTT AGG AAG ATT GCG TTT GCT CGG GAC TTG TGT
 G   Q   L   R   K   I   A   F   A   R   D   L   C
TAT AGG AGC TTC GGG TGG GAC AAT GTC AGG TGC ACA ATT
 Y   R   S   F   G   W   D   N   V   R   C   T   I
GCG GTT CAG GCG CGT GAC CTT TCG GCC CCG TGC CCT AAG
 A   V   Q   A   R   D   L   S   A   P   C   P   K
GCT TAT AAC ACC CAT GGT TGA CTT TGG TTT TGT GTT GGT
 A   Y   N   T   H   G   *
TTGATTTATGTCCACACAATATTGAACTGAATAACCATGGAAGGCACTACGTTCAGCT
CCCTTGTTGTGGGGGCAAAGTGCAGTATTTATTTCTTATCCCATGTACTTTTTGATT
TAATTTATTATTGATTAAATTTTGTTAGTTGGGTGTCTCTATAGCAAGTTTATATAAT
AAAAAAAAA
```

FIGURE 10E

```
TGC CCA CCG TGG ATG GAC
 C   P   P   W   M   D
TTC CCT AGG CTG CCG CGT
 F   P   R   L   P   R
AAG AAG CAC GGG ATG CCG
 K   K   H   G   M   P
CGG ACG CTG AGG GAT GCG
 R   T   L   R   D   A
AAA CTT GGG TAT GGG GAA
 K   L   G   Y   G   E
TGG AGG ATC TTC TTA TTA
 W   R   I   F   L   L
TAACTTTGCTAGCTGGTTGCGTT
ATTGTTCTTATTCGTATCATAAA
ACTGAGATATATTTTTTGGTAA
```

Evening Primrose Putative Δ⁶-Desaturase Hopwood Hydrophilicity Plot

PRODUCTION OF GAMMA LINOLENIC ACID BY A Δ 6-DESATURASE

CROSS REFERENCE TO RELATED APPLICATIONS

This is a divisional application of U.S. Ser. No. 09/685,775 filed on Oct. 10, 2000, now U.S. Pat. No. 6,683,232 which is a divisional application of U.S. Ser. No. 08/934,254 filed on Sep. 19, 1997, now U.S. Pat. No. 6,355,861 which is a continuation-in-part of U.S. Ser. No. 08/789,936 filed Jan. 28, 1997, now U.S. Pat. No. 5,789,220, which is a continuation-in-part of U.S. Ser. No. 08/307,382 filed Sep. 14, 1994, now U.S. Pat. No. 5,552,306, which is a continuation of U.S. Ser. No. 07/959,952 filed Oct. 13, 1992, abandoned, which is a continuation-in-part of U.S. Ser. No. 07/817,919 filed Jan. 8, 1992, abandoned, which is a continuation-in-part application of U.S. Ser. No. 07/774,475 filed Oct. 10, 1991, abandoned.

FIELD OF THE INVENTION

Linoleic acid (18:2) (LA) is transformed into gamma linolenic acid (18:3) (GLA) by the enzyme Δ6-desaturase. When this enzyme, or the nucleic acid encoding it, is transferred into LA-producing cells, GLA is produced. The present invention provides nucleic acids comprising the Δ6-desaturase gene. More specifically, the nucleic acids comprise the promoters, coding regions and termination regions of the Δ6-desaturase genes. The present invention is further directed to recombinant constructions comprising a Δ6-desaturase coding region in functional combination with heterologous regulatory sequences. The nucleic acids and recombinant constructions of the instant invention are useful in the production of GLA in transgenic organisms.

BACKGROUND OF THE INVENTION

Unsaturated fatty acids such as linoleic ($C_{18}\Delta^{9,12}$) and α-linolenic ($C_{18}\Delta^{9,12,15}$) acids are essential dietary constituents that cannot be synthesized by vertebrates since vertebrate cells can introduce double bonds at the $\Delta^9$ position of fatty acids but cannot introduce additional double bonds between the $\Delta^9$ double bond and the methyl-terminus of the fatty acid chain. Because they are precursors of other products, linoleic and α-linolenic acids are essential fatty acids, and are usually obtained from plant sources. Linoleic acid can be converted by mammals into γ-linolenic acid (GLA, $C_{18}\Delta^{6,9,12}$) which can in turn be converted to arachidonic acid (20:4), a critically important fatty acid since it is an essential precursor of most prostaglandins.

The dietary provision of linoleic acid, by virtue of its resulting conversion to GLA and arachidonic acid, satisfies the dietary need for GLA and arachidonic acid. However, a relationship has been demonstrated between consumption of saturated fats and health risks such as hypercholesterolemia, atherosclerosis and other clinical disorders which correlate with susceptibility to coronary disease, while the consumption of unsaturated fats has been associated with decreased blood cholesterol concentration and reduced risk of atherosclerosis. The therapeutic benefits of dietary GLA may result from GLA being a precursor to arachidonic acid and thus subsequently contributing to prostaglandin synthesis. Accordingly, consumption of the more unsaturated GLA, rather than linoleic acid, has potential health benefits. However, GLA is not present in virtually any commercially grown crop plant.

Linoleic acid is converted into GLA by the enzyme Δ6-desaturase. Δ6-desaturase, an enzyme of more than 350 amino acids, has a membrane-bound domain and an active site for desaturation of fatty acids. When this enzyme is transferred into cells which endogenously produce linoleic acid but not GLA, GLA is produced. The present invention, by providing genes encoding Δ6-desaturase, allows the production of transgenic organisms which contain functional Δ6-desaturase and which produce GLA. In addition to allowing production of large amounts of GLA, the present invention provides new dietary sources of GLA.

SUMMARY OF THE INVENTION

The present invention is directed to isolated Δ6-desaturase genes. Specifically, the isolated genes comprise the Δ6-desaturase promoters, coding regions, and termination regions.

The present invention is further directed to expression vectors comprising the Δ6-desaturase promoter, coding region and termination region.

Yet another aspect of this invention is directed to expression vectors comprising a Δ6-desaturase coding region in functional combination with heterologous regulatory regions, i.e. elements not derived from the Δ6-desaturase gene.

Cells and organisms comprising the vectors of the present invention, and progeny of such organisms, are also provided by the present invention.

A further aspect of the present invention provides isolated bacterial Δ6-desaturase. Isolated plant Δ6-desaturases are also provided.

Yet another aspect of this invention provides a method for producing plants with increased gamma linolenic acid content.

A method for producing chilling tolerant plants is also provided by the present invention.

BRIEF DESCRIPTION OF THE DRAWINGS

FIGS. 5A(1) and 5A(2) depict the DNA sequence of a Δ6-desaturase cDNA isolated from borage.

FIGS. 5B(1) and 5B(2) depict the protein sequence of the open reading frame in the isolated borage Δ6-desaturase cDNA. Three amino acid motifs characteristic of desaturases are indicated in bold and underlined and are, in order, lipid box, metal box 1, and metal box 2.

FIG. 8(A and B) provides gas liquid chromatography profiles of mock transfected (FIG. 8A) and 221.Δ6.NOS transfected (FIG. 8B) carrot cells. The positions of 18:2, 18:3 α, and 18:3 γ (GLA) are indicated.

FIG. 10(A through F) provides the complete DNA sequence and deduced amino acid sequence of evening primrose Δ6-desaturase. A heme binding motif, HPGG, of cytochrome b5 proteins is indicated by underlined text. Three histine rich motifs (HRMs), GHDSGH, HNAHH and FOLEHH are also underlined. The motifs in this sequence are identical to those found in borage Δ6-desaturase with the exception of those that are italicized (S 161 and L 374).

DETAILED DESCRIPTION OF THE INVENTION

Figure 1A:
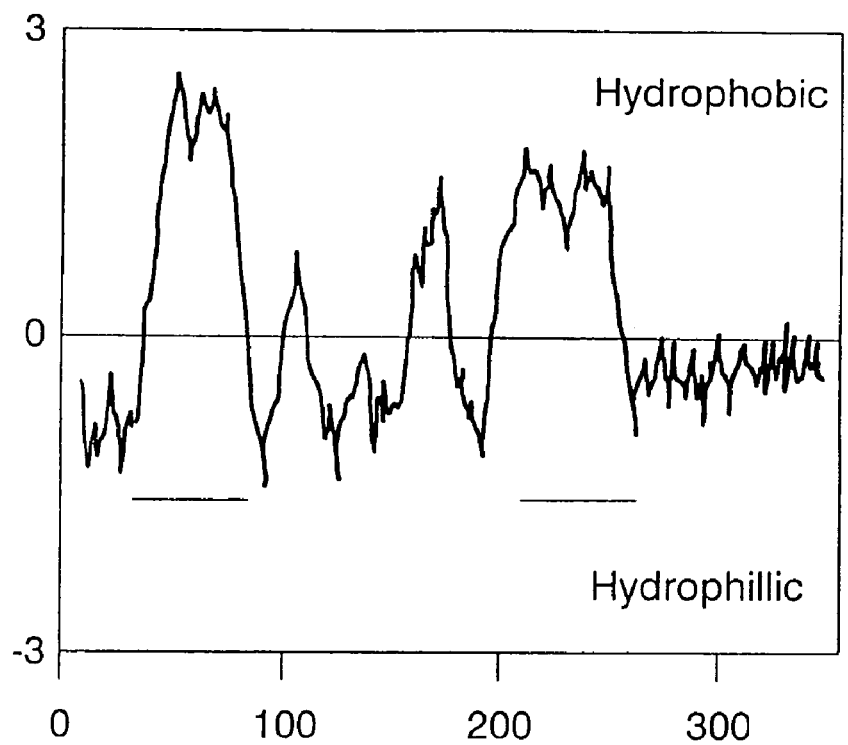
FIG. 1(A and B) depicts the hydropathy profiles of the deduced amino acid sequences of Synechocystis Δ6-desaturase (FIG. 1A) and Δ12-desaturase (FIG. 1B). Putative membrane spanning regions are indicated by solid bars. Hydrophobic index was calculated for a window size of 19 amino acid residues (Kyte, et al. (1982) J. Molec. Biol. 157).

The present invention provides isolated nucleic acids encoding Δ6-desaturase. To identify a nucleic acid encoding Δ6-desaturase, DNA is isolated from an organism which produces GLA. Said organism can be, for example, an animal cell, certain fungi (e.g. Mortierell), certain bacteria (e.g. Synechocystis) or certain plants (borage, Oenothera, currants). The isolation of genomic DNA can be accomplished by a variety of methods well-known to one of ordinary skill in the art, as exemplified by Sambrook et al. (1989) in Molecular Cloning: A Laboratory Manual, Cold Spring Harbor, N.Y. The isolated DNA is fragmented by physical methods or enzymatic digestion and cloned into an appropriate vector, e.g. a bacteriophage or cosmid vector, by any of a variety of well-known methods which can be found in references such as Sambrook et al. (1989). Expression vectors containing the DNA of the present invention are specifically contemplated herein. DNA encoding Δ-desaturase can be identified by gain of function analysis. The vector containing fragmented DNA is transferred, for example by infection, transconjugation, transfection, into a host organism that produces linoleic acid but not GLA. As used herein, "transformation" refers generally to the incorporation of foreign DNA into a host cell. Methods for introducing recombinant DNA into a host organism are known to one of ordinary skill in the art and can be found, for example, in Sambrook et al. (1989). Production of GLA by these organisms (i.e., gain of function) is assayed, for example by gas chromatography or other methods known to the ordinarily skilled artisan. Organisms which are induced to produce GLA, i.e. have gained function by the introduction of the vector, are identified as expressing DNA encoding Δ-desaturase, and said DNA is recovered from the organisms. The recovered DNA can again be fragmented, cloned with expression vectors, and functionally assessed by the above procedures to define with more particularity the DNA encoding Δ6-desaturase.

As an example of the present invention, random DNA is isolated from the cyanobacteria Synechocystis Pasteur Culture Collection (PCC) 6803, American Type. Culture Collection (ATCC) 27184, cloned into a cosmid vector, and introduced by transconjugation into the GLA-deficient Cyanobacterium Anabaena strain PCC 7120, ATCC 27893. Production of GLA from Anabaena linoleic acid is monitored by gas chromatography and the corresponding DNA fragment is isolated.

The isolated DNA is sequenced by methods well-known to one of ordinary skill in the art as found, for example, in Sambrook et al. (1989).

In accordance with the present invention, DNA molecules comprising Δ6-desaturase genes have been isolated. More particularly, a 3.588 kilobase (kb) DNA comprising a Δ6-desaturase gene has been isolated from the cyanobacteria Synechocystis. The nucleotide sequence of the 3.588 kb DNA was determined and is shown in SEQ ID NO:1. Open reading frames defining potential coding regions are present from nucleotide 317 to 1507 and from nucleotide 2002 to 3081. To define the nucleotides responsible for encoding Δ6-desaturase, the 3.588 kb fragment that confers Δ6-desaturase activity is cleaved into two subfragments, each of which contains only one open reading frame. Fragment ORF1 contains nucleotides 1 through 1704, while fragment ORF2 contains nucleotides 1705 through 3588. Each fragment is subcloned in both forward and reverse orientations into a conjugal expression vector (AM542, Wolk et al. [1984] Proc. Natl. Acad. Sci. USA 81, 1561) that contains a cyanobacterial carboxylase promoter. The resulting constructs (i.e. ORF1(F), ORF1(R), ORF2(F) and ORF2(R)) are conjugated to wild-type Anabaena PCC 7120 by standard methods (see, for example, Wolk et al. (1984) Proc. Natl. Acad. Sci. USA 81, 1561). Conjugated cells of Anabaena are identified as Neo$^R$ green colonies on a brown background of dying non-conjugated cells after two weeks of growth on selective media (standard mineral media BG11N+containing 30 μg/ml of neomycin according to Rippka et al., (1979) J. Gen Microbiol. 111, 1). The green colonies are selected and grown in selective liquid media (BG11N+with 15 μg/ml neomycin). Lipids are extracted by standard methods (e.g. Dahmer et al., (1989) Journal of American Oil Chemical Society 66, 543) from the resulting transconjugants containing the forward and reverse oriented ORF1 and ORF2 constructs. For comparison, lipids are also extracted from wild-type cultures of Anabaena and Synechocystis. The fatty acid methyl esters are analyzed by gas liquid chromatography (GLC), for example with a Tracor-560 gas liquid chromatograph equipped with a hydrogen flame ionization detector and a capillary column. The results of GLC analysis are shown in Table 1.

TABLE 1

Occurrence of C18 fatty acids in wild-type and transgenic cyanobacteria

| SOURCE | 18:0 | 18:1 | 18:2 | γ 18:2 | α 18:3 | 18:4 |
|---|---|---|---|---|---|---|
| Anabaena (wild type) | + | + | + | − | + | − |
| Anabaena + ORF1 (F) | + | + | + | − | + | − |
| Anabaena + ORF1 (R) | + | + | + | − | + | − |
| Anabaena + ORF2 (F) | + | + | + | + | + | + |
| Anabaena + ORF2 (R) | + | + | + | − | + | − |
| Synechocystis (wild type) | + | + | + | + | − | − |

Figure 1B:
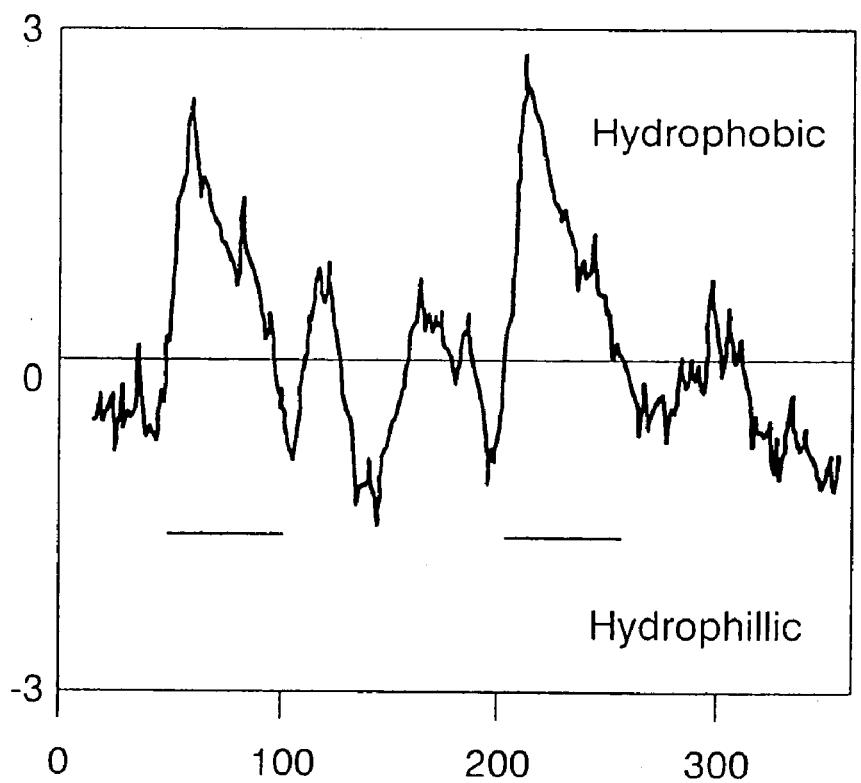

As assessed by GLC analysis, GLA deficient *Anabaena* gain the function of GLA production when the construct containing ORF2 in forward orientation is introduced by transconjugation. Transconjugants containing constructs with ORF2 in reverse orientation to the carboxylase promoter, or ORF1 in either orientation, show no GLA production. This analysis demonstrates that the single open reading frame (ORF2) within the 1884 bp fragment encodes Δ6-desaturase. The 1884 bp fragment is shown as SEQ ID NO:3. This is substantiated by the overall similarity of the hydropathy profiles between Δ6-desaturase and Δ12-desaturase [Wada et al. (1990) *Nature* 347] as shown in FIG. 1 as (A) and (B), respectively.

Also in accordance with the present invention, a cDNA comprising a Δ6-desaturase gene from borage (*Borago officinalis*) has been isolated. The nucleotide sequence of the 1.685 kilobase (kb) cDNA was determined and is shown in FIG. 5A (SEQ ID NO: 4). The ATG start codon and stop codon are underlined. The amino acid sequence corresponding to the open reading frame in the borage delta 6-desaturase is shown in FIG. 5B (SEQ ID NO: 5).

Additionally, the present invention provides a Δ6-desaturase gene from evening primrose (*Oenothera biennis*). The nucleotide sequence of the 1.687 kb cDNA was determined and is depicted in FIG. 10 (SEQ ID NO:26). Also shown in FIG. 10 is the deduced amino acid sequence of evening primrose Δ6-desaturase.

Isolated nucleic acids encoding Δ6-desaturase can be identified from other GLA-producing organisms by the gain of function analysis described above, or by nucleic acid hybridization techniques using the isolated nucleic acid which encodes Synechocystis, borage, or evening primrose Δ6-desaturase as a hybridization probe. Both methods are known to the skilled artisan and are contemplated by the present invention. The hybridization probe can comprise the entire DNA sequence disclosed as SEQ. ID NO:1 or SEQ. ID NO:4, or a restriction fragment or other DNA fragment thereof, including an oligonucleotide probe. Methods for cloning homologous genes by cross-hybridization are known to the ordinarily skilled artisan and can be found, for example, in Sambrook (1989) and Beltz et al. (1983) *Methods in Enzymology* 100, 266.

In another method of identifying a delta 6-desaturase gene from an organism producing GLA, a cDNA library is made from poly-A$^+$ RNA isolated from polysomal RNA. In order to eliminate hyper-abundant expressed genes from the cDNA population, cDNAs or fragments thereof corresponding to hyper-abundant cDNAs genes are used as hybridization probes to the cDNA library. Non hybridizing plaques are excised and the resulting bacterial colonies are used to inoculate liquid cultures and sequenced. For example, as a means of eliminating other seed storage protein cDNAs from a cDNA library made from borage polysomal RNA, cDNAs corresponding to abundantly expressed seed storage proteins are first hybridized to the cDNA library. The "subtracted" DNA library is then used to generate expressed sequence tags (ETSs) and such tags are used to scan a data base such as GenBank to identify potential desaturates.

Using another method, an evening primrose cDNA may be isolated by first synthesizing sequences from the borage Δ6-desaturase gene and then using these sequences as primers in a PCR reaction with the evening primrose cDNA library serving as template. PCR fragments of expected size may then be used to screen an evening primrose cDNA library. Hybridizing clones may then be sequenced and compared to the borage cDNA sequence to determine if the hybridizing clone represents an evening primrose Δ6-desatuase gene.

Transgenic organisms which gain the function of GLA production by introduction of DNA encoding Δ6-desaturase also gain the function-of octadecatetraeonic acid ($18:4^{\Delta 6,9,12,15}$) production. Octadecatetraeonic acid is present normally in fish oils and in some plant species of the Boraginaceae family (Craig et al. [1964] *J. Amer. Oil Chem. Soc.* 1, 209-211; Gross et al. [1976] *Can. J. Plant Sci.* 5, 659-664). In the transgenic organisms of the present invention, octadecatetraenoic acid results from further desaturation of α-linolenic acid by Δ6-desaturase or desaturation of GLA by Δ15-desaturase.

The 359 amino acids encoded by ORF2, i.e. the open reading frame encoding Synechocystis Δ6-desaturase, are shown as SEQ. ID NO:2. The open reading frame encoding the borage Δ6-desaturase is shown in SEQ ID NO: 5. The present invention further contemplates other nucleotide sequences which encode the amino acids of SEQ ID NO:2 and SEQ ID NO: 5. It is within the ken of the ordinarily skilled artisan to identify such sequences which result, for example, from the degeneracy of the genetic code. Furthermore, one of ordinary skill in the art can determine, by the gain of function analysis described hereinabove, smaller subfragments of the fragments containing the open reading frames which encode Δ6-desaturases.

The present invention contemplates any such polypeptide fragment of Δ6-desaturase and the nucleic acids therefor which retain activity for converting LA to GLA.

In another aspect of the present invention, a vector containing a nucleic acid of the present invention or a smaller fragment containing the promoter, coding sequence and termination region of a Δ6-desaturase gene is transferred into an organism, for example, cyanobacteria, in which the Δ6-desaturase promoter and termination regions are functional. Accordingly, organisms producing recombinant Δ6-desaturase are provided by this invention. Yet another aspect of this invention provides isolated Δ6-desaturase, which can be purified from the recombinant organisms by standard methods of protein purification. (For example, see Ausubel et al. [1987] *Current Protocols in Molecular Biology*, Green Publishing Associates, New York).

Vectors containing DNA encoding Δ6-desaturase are also provided by the present invention. It will be apparent to one of ordinary skill in the art that appropriate vectors can be constructed to direct the expression of the Δ6-desaturase coding sequence in a variety of organisms. Replicable expression vectors are particularly preferred. Replicable expression vectors as described herein are DNA or RNA molecules engineered for controlled expression of a desired gene, i.e. the Δ6-desaturase gene. Preferably the vectors are plasmids, bacteriophages, cosmids or viruses. Shuttle vectors, e.g. as described by Wolk et al. (1984) *Proc. Natl. Acad. Sci. USA,* 1561-1565 and Bustos et al. (1991) *J. Bacteriol.* 174, 7525-7533, are also contemplated in accordance with the present invention. Sambrook et al. (1989), Goeddel, ed. (1990) *Methods in Enzymology* 185 Academic Press, and Perbal (1988) *A Practical Guide to Molecular Cloning*, John Wiley and Sons, Inc., provide detailed reviews of vectors into which a nucleic acid encoding the present Δ6-desaturase can be inserted and expressed. Such vectors also contain nucleic acid sequences which can effect expression of nucleic acids encoding Δ6-desaturase. Sequence elements capable of effecting expression of a gene product include promoters, enhancer elements, upstream activating sequences, transcription termination signals and polyadenylation sites. The upstream 5' untranslated region of the evening primrose Δ6-desaturase gene as depicted in FIG. 10 may also be used. Both constitutive and tissue specific promoters are contemplated. For transformation of plant cells, the cauliflower mosaic virus (CaMV) 35S promoter, other constitutive promoters and promoters which are regulated during plant seed maturation are of particular interest. All such promoter and transcriptional regulatory elements, singly or in combination, are contemplated for use in the present replicable expression vectors and are known to one of ordinary skill in the art. The CaMV 35S promoter is described, for example, by Restrepo et al. (1990) *Plant Cell* 2, 987. Genetically engineered and mutated regulatory sequences are also contemplated.

The ordinarily skilled artisan can determine vectors and regulatory elements suitable for expression in a particular host cell. For example, a vector comprising the promoter from the gene encoding the carboxylase of *Anabaena* operably linked to the coding region of Δ6-desaturase and further operably linked to a termination signal from *Synechocystis* is appropriate for expression of Δ6-desaturase in cyanobacteria. "Operably linked" in this context means that the promoter and terminator sequences effectively function to regulate transcription. As a further example, a vector appropriate for expression of Δ6-desaturase in transgenic plants can comprise a seed-specific promoter sequence derived from helianthinin, napin, or glycinin operably linked to the Δ6-desaturase coding region and further operably linked to a seed termination signal or the nopaline synthase termination signal. As a still further example, a vector for use in expression of Δ6-desaturase in plants can comprise a constitutive promoter or a tissue specific promoter operably linked to the Δ6-desaturase coding region and further operably linked to a constitutive or tissue specific terminator or the nopaline synthase termination signal.

In particular, the helianthinin regulatory elements disclosed in applicant's copending U.S. application Ser. No. 682,354, filed Apr. 8, 1991 and incorporated herein by reference, are contemplated as promoter elements to direct the expression of the Δ6-desaturases of the present invention. The albumin regulatory elements disclosed in applicant's copending U.S. application Ser. No. 08/831,570 and the oleosin regulatory elements disclosed in applicant's copending U.S. application Ser. No. 08/831,575 (both applications filed Apr. 9, 1997), and incorporated herein by reference, are also contemplated as elements to direct the expression of the Δ6-desaturases of the present invention.

Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

Standard techniques for the construction of such hybrid vectors are well-known to those of ordinary skill in the art and can be found in references such as Sambrook et al. (1989), or any of the myriad of laboratory manuals on recombinant DNA technology that are widely available. A variety of strategies are available for ligating fragments of DNA, the choice of which depends on the nature of the termini of the DNA fragments. It is further contemplated in accordance with the present invention to include in the hybrid vectors other nucleotide sequence elements which facilitate cloning, expression or processing, for example sequences encoding signal peptides, a sequence encoding KDEL or related sequence, which is required for retention of proteins in the endoplasmic reticulum or sequences encoding transit peptides which direct Δ6-desaturase to the chloroplast. Such sequences are known to one of ordinary skill in the art. An optimized transit peptide is described, for example, by Van den Broeck et al. (1985) *Nature* 313, 358. Prokaryotic and eukaryotic signal sequences are disclosed, for example, by Michaelis et al. (1982) *Ann. Rev. Microbiol.* 36, 425.

A further aspect of the instant invention provides organisms other than cyanobacteria or plants which contain the DNA encoding the Δ6-desaturase of the present invention. The transgenic organisms contemplated in accordance with the present invention include bacteria, cyanobacteria, fungi, and plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989).

A variety of plant transformation methods are known. The Δ6-desaturase gene can be introduced into plants by a leaf disk transformation-regeneration procedure as described by Horsch et al. (1985) *Science* 227, 1229. Other methods of transformation, such as protoplast culture (Horsch et al. (1984) *Science* 223, 496; DeBlock et al. (1984) *EMBO J.* 2, 2143; Barton et al. (1983) *Cell* 2, 1033) can also be used and are within the scope of this invention. In a preferred embodiment plants are transformed with *Agrobacterium*-derived vectors such as those described in Klett et al. (1987) *Annu. Rev. Plant Physiol.* 38:467. However, other methods are available to insert the Δ6-desaturase genes of the present invention into plant cells. Such alternative methods include biolistic approaches (Klein et al. (1987) *Nature* 327, 70), electroporation, chemically-induced DNA uptake, and use of viruses or pollen as vectors.

When necessary for the transformation method, the Δ6-desaturase genes of the present invention can be inserted into a plant transformation vector, e.g. the binary vector described by Bevan (1984) *Nucleic Acids Res.* 12, 8111. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors the tumor-inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transformation of sequences bordered by the T-region into the nuclear genomes of plants.

Surface-sterilized leaf disks are inoculated with the "disarmed" foreign DNA-containing *A. tumefaciens*, cultured for two days, and then transferred to antibiotic-containing medium. Transformed shoots are selected after rooting in medium containing the appropriate antibiotic, transferred to soil and regenerated.

Another aspect of the present invention provides transgenic plants or progeny of these plants containing the isolated DNA of the invention. Both monocotyledenous and dicotyledenous plants are contemplated. Plant cells are transformed with the isolated DNA encoding Δ6-desaturase by any of the plant transformation methods described above. The transformed plant cell, usually in a callus culture or leaf disk, is regenerated into a complete transgenic plant by methods well-known to one of ordinary skill in the art (e.g. Horsch et al. (1985) *Science* 227, 1129). In a preferred embodiment, the transgenic plant is sunflower, oil seed rape, maize, tobacco, peanut or soybean. Since progeny of transformed plants inherit the DNA encoding Δ6-desaturase, seeds or cuttings from transformed plants are used to maintain the transgenic plant line.

The present invention further provides a method for providing transgenic plants with an increased content of GLA. This method includes introducing DNA encoding Δ6-desaturase into plant cells which lack or have low levels of GLA but contain LA, and regenerating plants with increased GLA content from the transgenic cells. In particular, commercially grown crop plants are contemplated as the transgenic organism, including, but not limited to, sunflower, soybean, oil seed rape, maize, peanut and tobacco.

The present invention further provides a method for providing transgenic organisms which contain GLA. This method comprises introducing DNA encoding Δ6-desaturase into an organism which lacks or has low levels of GLA, but contains LA. In another embodiment, the method comprises introducing one or more expression vectors which comprise DNA encoding Δ12-desaturase and Δ6-desaturase into organisms which are deficient in both GLA and LA. Accordingly, organisms deficient in both LA and GLA are induced to produce LA by the expression of Δ12-desaturase, and GLA is then generated due to the expression of Δ6-desaturase. Expression vectors comprising DNA encoding Δ12-desaturase, or Δ12-desaturase and Δ6-desaturase, can be constructed by methods of recombinant technology known to one of ordinary skill in the art (Sambrook et al., 1989) and the published sequence of Δ12-desaturase (Wada et al [1990] *Nature* (London) 347, 200-203. In addition, it has been discovered in accordance with the present invention that nucleotides 2002-3081 of SEQ. ID NO:1 encode cyanobacterial Δ12-desaturase. Accordingly, this sequence can be used to construct the subject expression vectors. In particular, commercially grown crop plants are contemplated as the transgenic organism, including, but not limited to, sunflower, soybean, oil seed rape, maize, peanut and tobacco.

The present invention is further directed to a method of inducing chilling tolerance in plants. Chilling sensitivity may be due to phase transition of lipids in cell membranes. Phase transition temperature depends upon the degree of unsaturation of fatty acids in membrane lipids, and thus increasing the degree of unsaturation, for example by introducing Δ6-desaturase to convert LA to GLA, can induce or improve chilling resistance. Accordingly, the present method comprises introducing DNA encoding Δ6-desaturase into a plant cell, and regenerating a plant with improved chilling resistance from said transformed plant cell. In a preferred embodiment, the plant is a sunflower, soybean, oil seed rape, maize, peanut or tobacco plant.

The following examples further illustrate the present invention.

EXAMPLE 1

Strains and Culture Conditions

Synechocystis (PCC 6803, ATCC 27184), *Anabaena* (PCC 7120, ATCC 27893) and Synechococcus (PCC 7942, ATCC 33912) were grown photoautotrophically at 30° C. in BG11N+ medium (Rippka et al. [1979] *J. Gen. Microbiol.* 111, 1-61) under illumination of incandescent lamps (60 $\mu E.m^{-2}.S^{-1}$). Cosmids and plasmids were selected and propagated in *Escherichia coli* strain DH5α on LB medium supplemented with antibiotics at standard concentrations as described by Maniatis et al. (1982) *Molecular Cloning: A Laboratory Manual*, Cold Spring Harbor Laboratory, Cold Spring, N.Y.

EXAMPLE 2

Construction of Synechocystis Cosmid Genomic Library

Total genomic DNA from Synechocystis (PCC 6803) was partially digested with Sau3A and fractionated on a sucrose gradient (Ausubel et al. [1987] *Current Protocols in Molecular Biology*, Greene Publishing Associates and Wiley Interscience, New York). Fractions containing 30 to 40 kb DNA fragments were selected and ligated into the dephosphorylated BamHI site of the cosmid vector, pDUCA7 (Buikema et al. [1991] *J. Bacteriol.* 173, 1879-1885). The ligated DNA was packaged in vitro as described by Ausubel et al. (1987), and packaged phage were propagated in *E. coli* DH5α containing the AvaI and Eco4711 methylase helper plasmid, pRL528 as described by Buikema et al. (1991). A total of 1152 colonies were isolated randomly and maintained individually in twelve 96-well microtiter plates.

EXAMPLE 3

Gain-of-Function Expression of GLA in *Anabaena*

*Anabaena* (PCC 7120), a filamentous cyanobacterium, is deficient in GLA but contains significant amounts of linoleic acid, the precursor for GLA (FIG. 2; Table 2). The Synechocystis cosmid library described in Example 2 was conjugated into *Anabaena* (PCC 7120) to identify transconjugants that produce GLA. *Anabaena* cells were grown to mid-log phase in BG11N+ liquid medium and resuspended in the same medium to a final concentration of approximately $2\times10^8$ cells per ml. A mid-log phase culture of *E. coli* RP4 (Burkardt et al. [1979] *J. Gen. Microbiol.* 114, 341-348) grown in LB containing ampicillin was washed and resuspended in fresh LB medium. *Anabaena* and RP4 were then mixed and spread evenly on BG11N+ plates containing 5% LB. The cosmid genomic library was replica plated onto LB plates containing 50 μg/ml kanamycin and 17.5 μg/ml chloramphenicol and was subsequently patched onto BG11N+ plates containing *Anabaena* and RP4. After 24 hours of incubation at 30° C., 30 μg/ml of neomycin was underlaid; and incubation at 30° C. was continued until transconjugants appeared.

Individual transconjugants were isolated after conjugation and grown in 2 ml BG11N+ liquid medium with 15 μg/ml neomycin. Fatty acid methyl esters were prepared from wild type cultures and cultures containing pools of ten transconjugants as follows. Wild type and transgenic cyanobacterial cultures were harvested by centrifugation and washed twice with distilled water. Fatty acid methyl esters were extracted from these cultures as described by Dahmer et al. (1989) *J. Amer. Oil. Chem. Soc.* 66, 543-548 and were analyzed by Gas Liquid Chromatography (GLC) using a Tracor-560 equipped with a hydrogen flame ionization detector and capillary column (30 m×0.25 mm bonded FSOT Superox II, Alltech Associates Inc., IL). Retention times and co-chromatography of standards (obtained from Sigma Chemical Co.) were used for identification of fatty acids. The average fatty acid composition was determined as the ratio of peak area of each C18 fatty acid normalized to an internal standard.

Representative GLC profiles are shown in FIG. 2. C18 fatty acid methyl esters are shown. Peaks were identified by comparing the elution times with known standards of fatty acid methyl esters and were confirmed by gas chromatography-mass spectrometry. Panel A depicts GLC analysis of fatty acids of wild type *Anabaena*. The arrow indicates the migration time of GLA. Panel B is a GLC profile of fatty acids of transconjugants of *Anabaena* with pAM542+1.8F. Two GLA producing pools (of 25 pools representing 250 transconjugants) were identified that produced GLA. Individual transconjugants of each GLA positive pool were analyzed for GLA production; two independent transconjugants, AS13 and AS75, one from each pool, were identified which expressed significant levels of GLA and which contained cosmids, cSy13 and cSy75, respectively (FIG. 3). The cosmids overlap in a region approximately 7.5 kb in length. A 3.5 kb NheI fragment of cSy75 was recloned in the vector pDUCA7 and transferred to *Anabaena* resulting in gain-of-function expression of GLA (Table 2).

Two NheI/Hind III subfragments (1.8 and 1.7 kb) of the 3.5 kb Nhe I fragment of cSy75-3.5 were subcloned into "pBLUESCRIPT" (Stratagene) (FIG. 3) for sequencing. Standard molecular biology techniques were performed as described by Maniatis et al. (1982) and Ausubel et al. (1987). Dideoxy sequencing (Sanger et al. [1977] *Proc. Natl. Acad. Sci. USA* 74, 5463-5467) of pBS1.8 was performed with "SEQUENASE" (United States Biochemical) on both strands by using specific oligonucleotide primers synthesized by the Advanced DNA Technologies Laboratory (Biology Department, Texas A & M University). DNA sequence analysis was done with the GCG (Madison, Wis.) software as described by Devereux et al. (1984) *Nucleic Acids Res.* 12, 387-395.

Both NheI/HindIII subfragments were transferred into a conjugal expression vector, AM542, in both forward and reverse orientations with respect to a cyanobacterial carboxylase promoter and were introduced into *Anabaena* by conjugation. Transconjugants containing the 1.8 kb fragment in the forward orientation (AM542-1.8F) produced significant quantities of GLA and octadecatetraenoic acid (FIG. 2; Table 2). Transconjugants containing other constructs, either reverse oriented 1.8 kb fragment or forward and reverse oriented 1.7 kb fragment, did not produce detectable levels of GLA (Table 2).

Figure 2B:
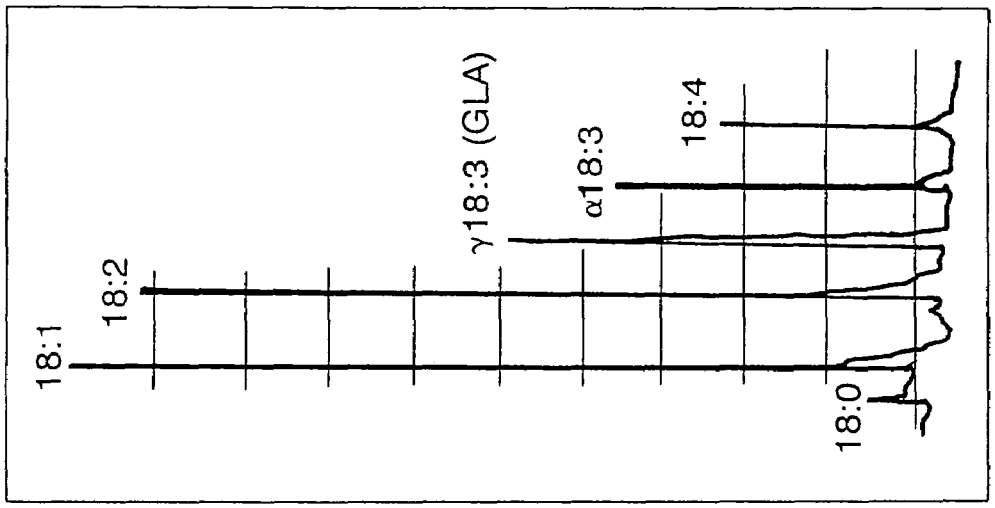
FIG. 2(A and B) provides gas liquid chromatography profiles of wild type (FIG. 2A) and transgenic (FIG. 2B) *Anabaena*.
Figure 2A:
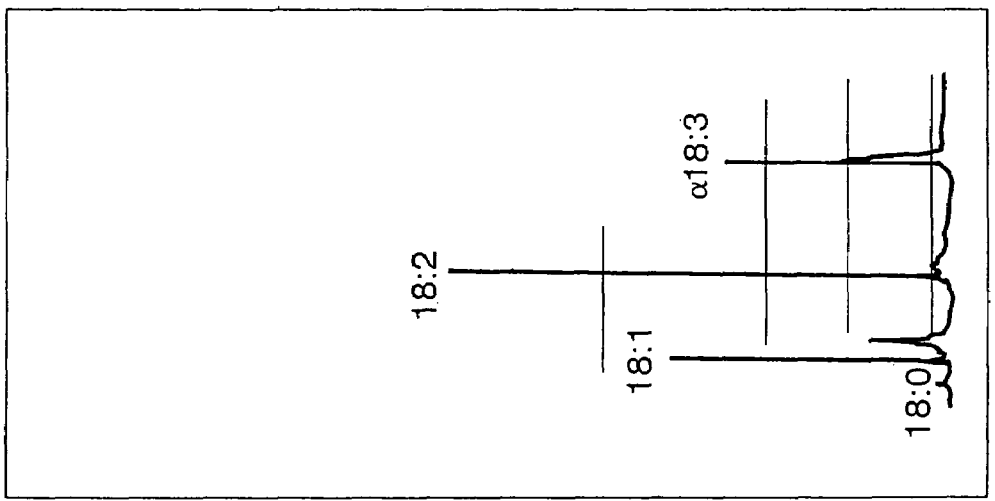
Figure 3:
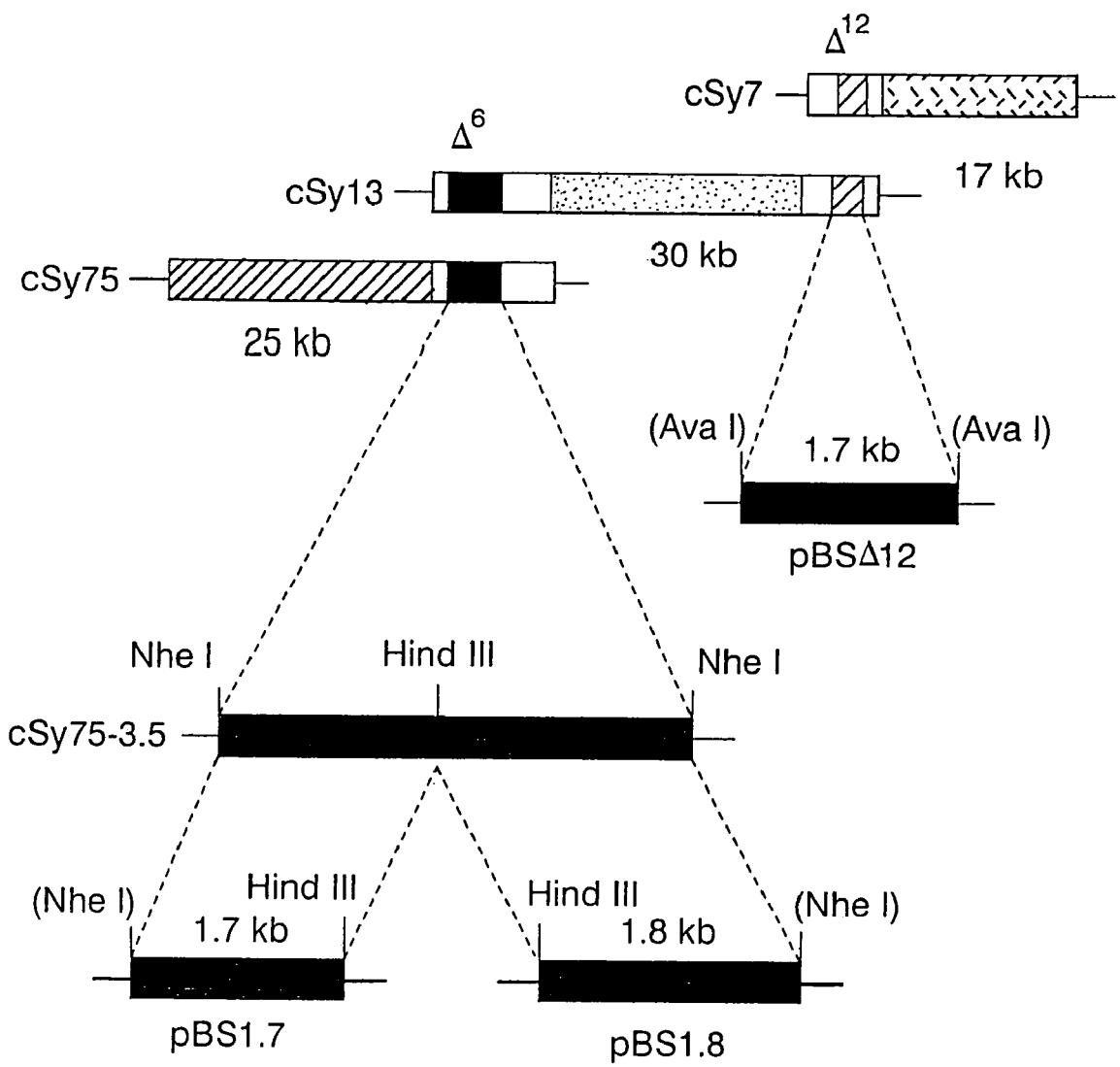
FIG. 3 is a diagram of maps of cosmid cSy75, cSy13 and Csy7 with overlapping regions and subclones. The origins of subclones of Csy75, Csy75-3.5 and Csy7 are indicated by the dashed diagonal lines. Restriction sites that have been inactivated are in parentheses.

FIG. 2 compares the C18 fatty acid profile of an extract from wild type *Anabaena* (FIG. 2A) with that of transgenic *Anabaena* containing the 1.8 kb fragment of cSy75-3.5 in the forward orientation (FIG. 2B). GLC analysis of fatty acid methyl esters from AM542-1.8F revealed a peak with a retention time identical to that of authentic GLA standard. Analysis of this peak by gas chromatography-mass spectrometry (GC-MS) confirmed that it had the same mass fragmentation pattern as a GLA reference sample. Transgenic *Anabaena* with altered levels of polyunsaturated fatty acids were similar to wild type in growth rate and morphology.

EXAMPLE 4

Transformation of Synechococcus with Δ6 and Δ12 Desaturase Genes

A third cosmid, cSy7, which contains a Δ12-desaturase gene, was isolated by screening the Synechocystis genomic library with a oligonucleotide synthesized from the published Synechocystis Δ12-desaturase gene sequence (Wada et al. [1990] *Nature* (London) 347, 200-203). A 1.7 kb AvaI fragment from this cosmid containing the Δ12-desaturase gene was identified and used as a probe to demonstrate that cSy13 not only contains a Δ6-desaturase gene but also a Δ12-desaturase gene (FIG. 3). Genomic Southern blot analysis further showed that both the Δ6-and Δ12-desaturase genes are unique in the Synechocystis genome so that both functional genes involved in C18 fatty acid desaturation are linked closely in the Synechocystis genome.

The unicellular cyanobacterium Synechococcus (PCC 7942) is deficient in both linoleic acid and GLA(3). The Δ12 and Δ6-desaturase genes were cloned individually and together into pAM854 (Bustos et al. [1991] *J. Bacteriol.* 174, 7525-7533), a shuttle vector that contains sequences necessary for the integration of foreign DNA into the genome of Synechococcus (Golden et al. [1987] *Methods in Enzymol.* 153, 215-231). Synechococcus was transformed with these gene constructs and colonies were selected. Fatty acid methyl esters were extracted from transgenic Synechococcus and analyzed by GLC.

Table 2 shows that the principal fatty acids of wild type Synechococcus are stearic acid (18:0) and oleic acid (18:1). Synechococcus transformed with pAM854-Δ12 expressed linoleic acid (18:2) in addition to the principal fatty acids. Transformants with pAM854-Δ6 and Δ12 produced both linoleate and GLA (Table 1). These results indicated that Synechococcus containing both Δ12- and Δ6-desaturase genes had gained the capability of introducing a second double bond at the Δ12 position and a third double bond at the Δ6 position of C18 fatty acids. However, no changes in fatty acid composition was observed in the transformant containing pAM854-Δ6, indicating that in the absence of substrate synthesized by the Δ12 desaturase, the Δ6-desaturase is inactive. This experiment further confirms that the 1.8 kb NheI/HindIII fragment (FIG. 3) contains both coding and promoter regions of the Synechocystis Δ6-desaturase gene. Transgenic Synechococcus with altered levels of polyunsaturated fatty acids were similar to wild type in growth rate and morphology.

TABLE 2

Composition of C18 Fatty Acids in Wild Type and Transgenic Cyanobacteria

| Strain | Fatty acid (%) | | | | | |
|---|---|---|---|---|---|---|
| | 18:0 | 18:1 | 18:2 | 18:3(α) | 18:3(γ) | 18:4 |
| Wild Type | | | | | | |
| Synechocystis (sp. PCC6803) | 13.6 | 4.5 | 54.5 | — | 27.3 | — |
| Anabaena (sp. PCC7120) | 2.9 | 24.8 | 37.1 | 35.2 | — | — |
| Synechococcus (sp. PCC7942) | 20.6 | 79.4 | — | — | — | — |
| Anabaena Transconjugants | | | | | | |
| cSy75 | 3.8 | 24.4 | 22.3 | 9.1 | 21.9 | 12.5 |

TABLE 2-continued

Composition of C18 Fatty Acids in Wild Type and Transgenic Cyanobacteria

| Strain | 18:0 | 18:1 | 18:2 | 18:3(α) | 18:3(γ) | 18:4 |
|---|---|---|---|---|---|---|
| cSy75-3.5 | 4.3 | 27.6 | 18.1 | 3.2 | 40.4 | 6.4 |
| pAM542 - 1.8F | 4.2 | 13.9 | 12.1 | 19.1 | 25.4 | 25.4 |
| pAM542 - 1.8R | 7.7 | 23.1 | 38.4 | 30.8 | — | — |
| pAM542 - 1.7F | 2.8 | 27.8 | 36.1 | 33.3 | — | — |
| pAM542 - 1.7R | 2.8 | 25.4 | 42.3 | 29.6 | — | — |
| Synechococcus Transformants | | | | | | |
| pAM854 | 27.8 | 72.2 | — | — | — | — |
| pAM854 - Δ$^{12}$ | 4.0 | 43.2 | 46.0 | — | — | — |
| pAM854 - Δ$^{6}$ | 18.2 | 81.8 | — | — | — | — |
| pAM854 - Δ$^{6}$ & Δ$^{12}$ | 42.7 | 25.3 | 19.5 | — | 16.5 | — |

18:0, stearic acid; 18:1, oleic acid; 18:2, linoleic add; 18:3(α), α-linoleic acid; 183(γ), γ-linolenic acid; 18:4, octadecatetraenoic acid

EXAMPLE 5

Nucleotide Sequenc of Δ6-desaturase

Figure 4B:
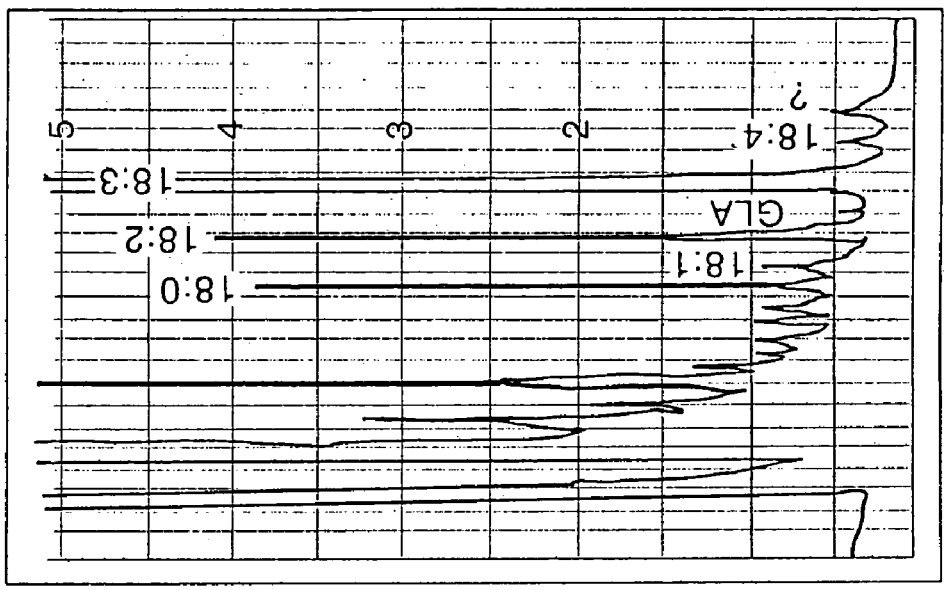
FIG. 4(A and B) provides gas liquid chromatography profiles of wild type (FIG. 4A) and transgenic (FIG. 4B) tobacco.
Figure 4A:
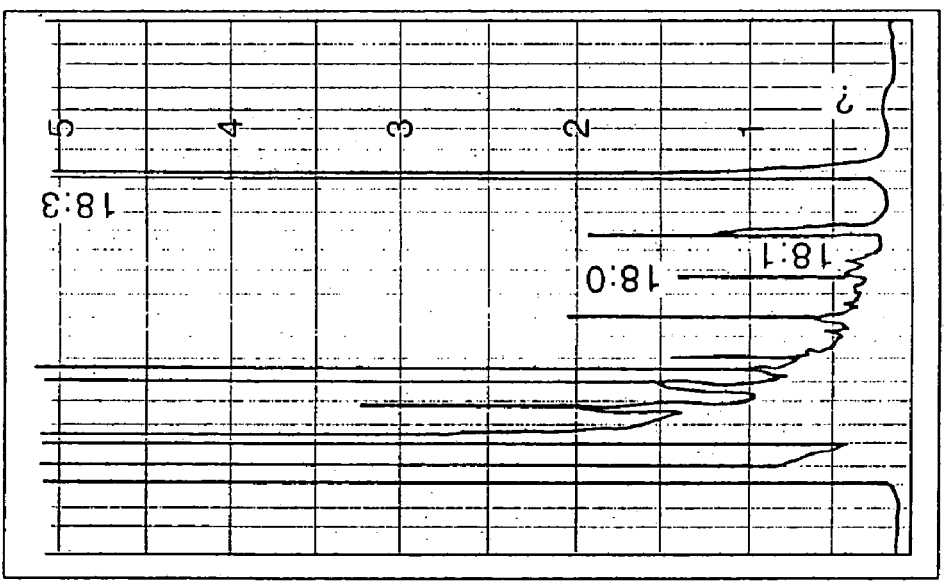

The nucleotide sequence of the 1.8 kb fragment of cSy75-3.5 including the functional Δ6-desaturase gene was determined. An open reading frame encoding a polypeptide of 359 amino acids was identified (FIG. 4). A Kyte-Doolittle hydropathy analysis (Kyte et al. [1982] *J. Mol. Biol.* 157, 105-132) identified two regions of hydrophobic amino acids that could represent transmembrane domains (FIG. 1A); furthermore, the hydropathic profile of the Δ6-desaturase is similar to that of the Δ12-desaturase gene (FIG. 1B; Wada et al.) and Δ9-desaturases (Thiede et al. [1986] *J. Biol. Chem.* 261, 13230-13235). However, the sequence similarity between the Synechocystis Δ6- and Δ12-desaturases is less than 40% at the nucleotide level and approximately 18% at the amino acid level.

EXAMPLE 6

Transf r of Cyanobacterial Δ$^{6}$-desaturas into Tobacco

The cyanobacterial Δ$^{6}$-desaturase gene was mobilized into a plant expression vector and transferred to tobacco using *Agrobacterium* mediated gene transfer techniques. To ensure that the transferred desaturase is appropriately expressed in leaves and developing seeds and that the desaturase gene product is targeted to the endoplasmic reticulum or the chloroplast, various expression cassettes with Synechocystis Δ-desaturase open reading frame (ORF) were constructed. Components of these cassettes include: (i) a 35S promoter or seed specific promoter derived from the sunflower helianthinin gene to drive Δ6-desaturase gene expression in all plant tissues or only in developing seeds respectively, (ii) a putative signal peptide either from carrot extension gene or sunflower helianthinin gene to target newly synthesized Δ6-desaturase into the ER, (iii) an ER lumen retention signal sequence (KDEL) at the COOH-terminal of the Δ6-desaturase ORF, and (iv) an optimized transit peptide to target Δ6 desaturase into the chloroplast. The 35S promoter is a derivative of pRTL2 described by Restrepo et al. (1990). The optimized transit peptide sequence is described by Van de Broeck et al. (1985). The carrot extensin signal peptide is described by Chen et al (1985) *EMBO J.* 9, 2145.

Transgenic tobacco plants were produced containing a chimeric cyanobacterial desaturase gene, comprised of the Synechocystis Δ6-desaturase gene fused to an endoplasmic reticulum retention sequence (KDEL) and extensin signal peptide driven by the CaMV 35S promoter. PCR amplifications of transgenic tobacco genomic DNA indicate that the Δ6-desaturase gene was incorporated into the tobacco genome. Fatty acid methyl esters of leaves of these transgenic tobacco plants were extracted and analyzed by Gas Liquid Chromatography (GLC). These transgenic tobacco accumulated significant amounts of GLA (FIG. 4). FIG. 4 shows fatty acid methyl esters as determined by GLC. Peaks were identified by comparing the elution times with known standards of fatty acid methyl ester. Accordingly, cyanobacterial genes involved in fatty acid metabolism can be used to generate transgenic plants with altered fatty acid compositions.

EXAMPLE 7

Construction of Borage cDNA Library

Membrane bound polysomes were isolated from borage seeds 12 days post pollination (12 DPP) using the protocol established for peas by Larkins and Davies (1975 *Plant Phys.* 55:749-756). RNA was extracted from the polysomes as described by Mechler (1987 Methods in Enzymology 152:241-248, Academic Press).

Poly-A+ RNA was isolated from the membrane bound polysomal RNA by use of Oligotex-dT beads (Qiagen). Corresponding cDNA was made using Stratagene's ZAP cDNA synthesis kit. The cDNA library was constructed in the lambda ZAP II vector (Stratagene) using the lambda ZAP II vector kit. The primary library was packaged in Gigapack II Gold packaging extract (Stratagene). The library was used to generate expressed sequence tags (ESTs), and sequences corresponding to the tags were used to scan the GenBank database.

EXAMPLE 8

Hybridization Protocol

Hybridization probes for screening the borage cDNA library were generated by using random primed DNA synthesis as described by Ausubel et al (1994 *Current Protocols in Molecular Biology*, Wiley Interscience, N.Y.) and corresponded to previously identified abundantly expressed seed storage protein cDNAs. Unincorporated nucleotides were removed by use of a G-50 spin column (Boehringer Mannheim). Probe was denatured for hybridization by boiling in a water bath for 5 minutes, then quickly cooled on ice. Filters for hybridization were prehybridized at 60° C. for 2-4 hours in prehybridization solution (6×SSC [Maniatis et al 1984 Molecular Cloning A Laboratory Manual, Cold Spring Harbor Laboratory], 1× Denharts Solution, 0.05% sodium pyrophosphate, 100 μg/ml denatured salmon sperm DNA). Denatured probe was added to the hybridization solution (6× SSC, 1× Denharts solution, 0.05% sodium pyrophosphate, 100 μg/ml denatured salmon sperm DNA) and incubated at 60° C. with agitation overnight. Filters were washed in 4×, 2×, and 1×SET washes for 15 minutes each at 60° C. A 20×SET stock solution is 3M NaCl, 0.4 M Tris base, 20 mM $Na_2EDTA$-$2H_2O$. The 4×SET wash was 4×SET, 12.5 mM $PO_4$, pH 6.8 and 0.2% SDS. The 2×SET wash was 2×SET, 12.5 mM $PO_4$, pH 6.8 and 0.2% SDS. The 1×SET wash was 1×SET, 12.5 mM $PO_4$, pH 6.8 and 0.2% SDS. Filters were allowed to air dry and were then exposed to X-ray film for 24 hours with intensifying screens at −80° C.

EXAMPLE 9

Random Sequencing of cDNAs from a Borage Seed (12 DPP) Membran-bound Polysomal Library The borage cDNA library was plated at low density (500 pfu on 150 mm petri dishes). Highly prevalent seed storage protein cDNAs were "subtracted" by screening with the previously identified corresponding cDNAs. Non-hybridizing plaques were excised using Stratagene's excision protocol and reagents. Resulting bacterial colonies were used to inoculate liquid cultures and were either sequenced manually or by an ABI automated sequencer. Each cDNA was sequenced once and a sequence tag generated from 200-300 base pairs. All sequencing was performed by cycle sequencing (Epicentre). Over 300 ESTs were generated. Each sequence tag was compared to GenBank database by BLASTX computer program and a number of lipid metabolism genes, including the Δ6-desaturase were identified.

Database searches with a cDNA clone designated mbp-65 using BLASTX with the GenBank database resulted in a significant match to the Synechocystis Δ6-desaturase. It was determined however, that this clone was not a full length cDNA. A full length cDNA was isolated using mbp-65 to screen the borage membrane-bound polysomal library. The sequence of the isolated cDNA was determined (FIG. 5A, SEQ ID NO:4) and the protein sequence of the open reading frame (FIG. 5B, SEQ ID NO:5) was compared to other known desaturases using Geneworks (IntelligGenetics) protein alignment program (FIG. 2). This alignment indicated that the cDNA was the borage Δ6-desaturase gene.

Figure 6:
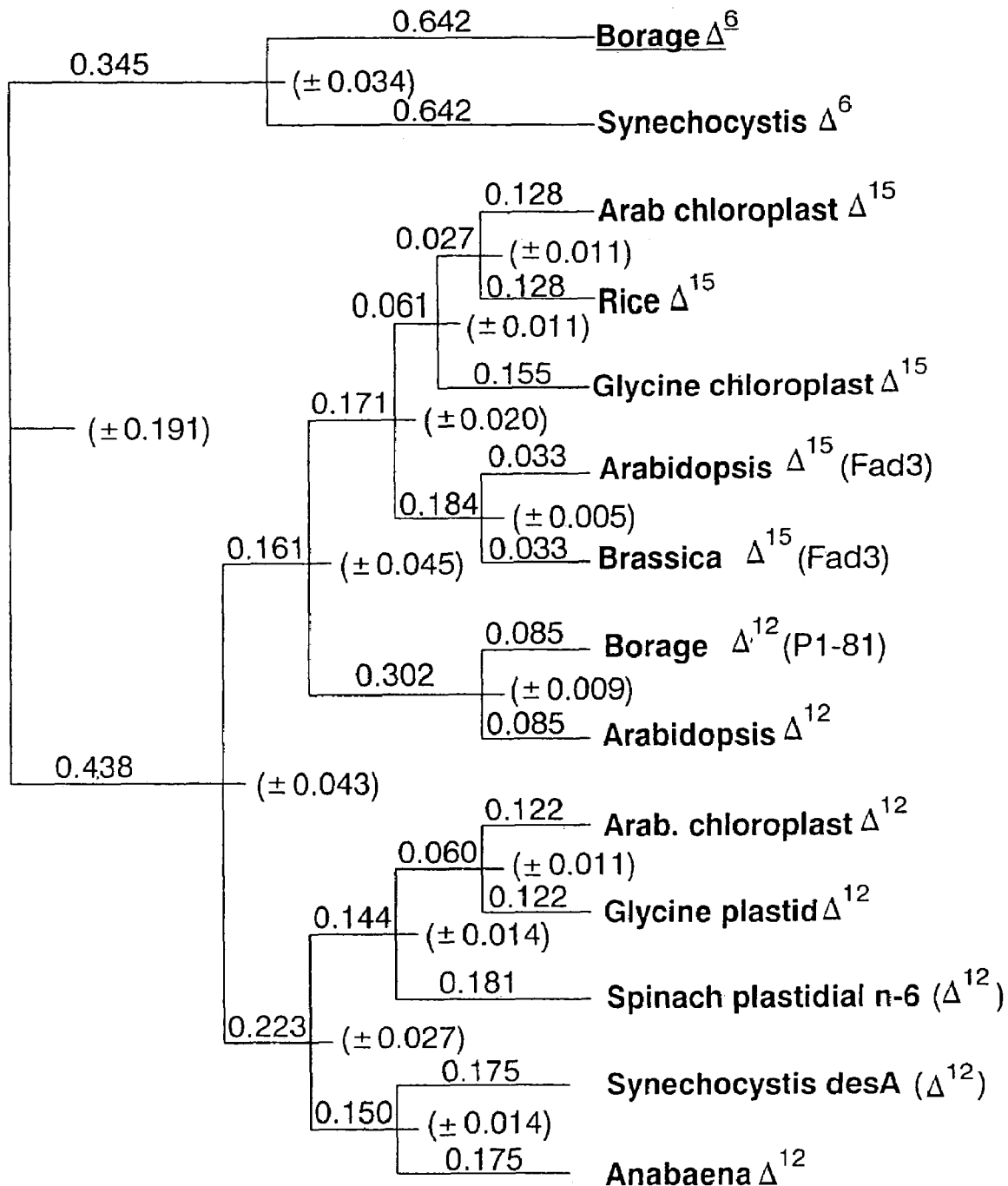
FIG. 6 is a dendrogram showing similarity of the borage Δ6-desaturase to other membrane-bound desaturases. The amino acid sequence of the borage Δ6-desaturase was compared to other known desaturases using Gene Works (IntelliGenetics). Numerical values correlate to relative phylogenetic distances between subgroups compared.

Although similar to other known plant desaturases, the borage delta 6-desaturase is distinct as indicated in the dendrogram shown in FIG. 6. Furthermore, comparison of the amino acid sequences characteristic of desaturases, particularly those proposed to be involved in metal binding (metal box 1 and metal box 2), illustrates the differences between the borage delta 6-desaturase and other plant desaturases (Table 3).

The borage delta 6-desaturase is distinguished from the cyanobacterial form not only in over all sequence (FIG. 6) but also in the lipid box, metal box 1 and metal box 2 amino acid motifs (Table 3). As Table 3 indicates, all three motifs are novel in sequence. Only the borage delta 6-desaturase metal box 2 showed some relationship to the Synechocystis delta-6 desaturase metal box 2.

In addition, the borage delta 6-desaturase is also distinct from another borage desaturase gene, the delta-12 desaturase. P1-81 is a full length cDNA that was identified by EST analysis and shows high similarity to the *Arabidopsis* delta-12 desaturase (Fad 2). A comparison of the lipid box, metal box 1 and metal box 2 amino acid motifs (Table 3) in borage delta 6 and delta-12 desaturases indicates that little homology exists in these regions. The placement of the two sequences in the dendrogram in FIG. 6 indicates how distantly related these two genes are.

TABLE 3

Comparison of common amino acid motifs in membrane-bound desaturases

| Desaturase | Amino Acid Motif | | |
|---|---|---|---|
| | Lipid Box | Metal Box 1 | Metal Box 2 |
| Borage Δ$^6$ | WIGHDAGH (SEQ. ID. NO: 6) | HNAHH (SEQ. ID. NO: 12) | FQIEHH (SEQ. ID. NO: 20) |
| Synechocystis Δ$^6$ | NVGHDANH (SEQ. ID. NO: 7) | HNYLHH (SEQ. ID. NO: 13) | HQVTHH (SEQ. ID. NO: 21) |
| Arab. chloroplast Δ$^{15}$ | VLGHDCGH (SEQ. ID. NO: 8) | HRTHH (SEQ. ID. NO: 14) | HVIHH (SEQ. ID. NO: 22) |
| Rice Δ$^{15}$ | VLGHDCGH (SEQ. ID. NO: 8) | HRTHH (SEQ. ID. NO: 14) | HVIHH (SEQ. ID. NO: 22) |
| Glycine chloroplast Δ$^{15}$ | VLGHDCGH (SEQ. ID. NO: 8) | HRTHH (SEQ. ID. NO: 14) | HVIHH (SEQ. ID. NO: 22) |
| Arab. fad3 (Δ$^{15}$) | VLGHDCGH (SEQ. ID. NO: 8) | HRTHH (SEQ. ID. NO: 14) | HVIHH (SEQ. ID. NO: 22) |
| Brassica fad3 (Δ$^{15}$) | VLGHDCGH (SEQ. ID. NO: 8) | HRTHH (SEQ. ID. NO: 14) | HVIHH (SEQ. ID. NO: 22) |
| Borage Δ$^{12}$ (P1-81)* | VIAHECGH (SEQ. ID. NO: 9) | HRRHH (SEQ. ID. NO: 15) | HVAHH (SEQ. ID. NO: 23) |
| Arab. fad2 (Δ$^{12}$) | VIAHECGH (SEQ. ID. NO: 9) | HRRHH (SEQ. ID. NO: 15) | HVAHH (SEQ. ID. NO: 23) |
| Arab. chloroplast Δ$^2$ | VIGHDCAH (SEQ. ID. NO: 10) | HDRHH (SEQ. ID. NO: 16) | HIPHH (SEQ. ID. NO: 24) |
| Glycine plastid Δ$^{12}$ | VIGHDCAH (SEQ. ID. NO: 10) | HDRHH (SEQ. ID. NO: 16) | HIPHM (SEQ. ID. NO: 24) |
| Spinach plastidial n-6 | VIGHDCAH (SEQ. ID. NO: 10) | HDQHH (SEQ. ID. NO: 17) | HIPHH (SEQ. ID. NO: 24) |
| Synechocystis Δ$^{12}$ | VVGHDCGH (SEQ. ID. NO: 11) | HDHHH (SEQ. ID. NO: 18) | HIPHH (SEQ. ID. NO: 24) |
| Anabaena Δ$^{12}$ | VLGHDCGH (SEQ. ID. NO: 8) | HNHHH (SEQ. ID. NO: 19) | HVPHH (SEQ. ID. NO: 25) |

*P1-81 is a full length cDNA which was identified by EST analysis and shows high similarity to the Arbidopsis Δ12 desaturase (fad2)

EXAMPLE 10

Construction of 222.1Δ$^6$NOS for Transient and Expression

Figure 7:
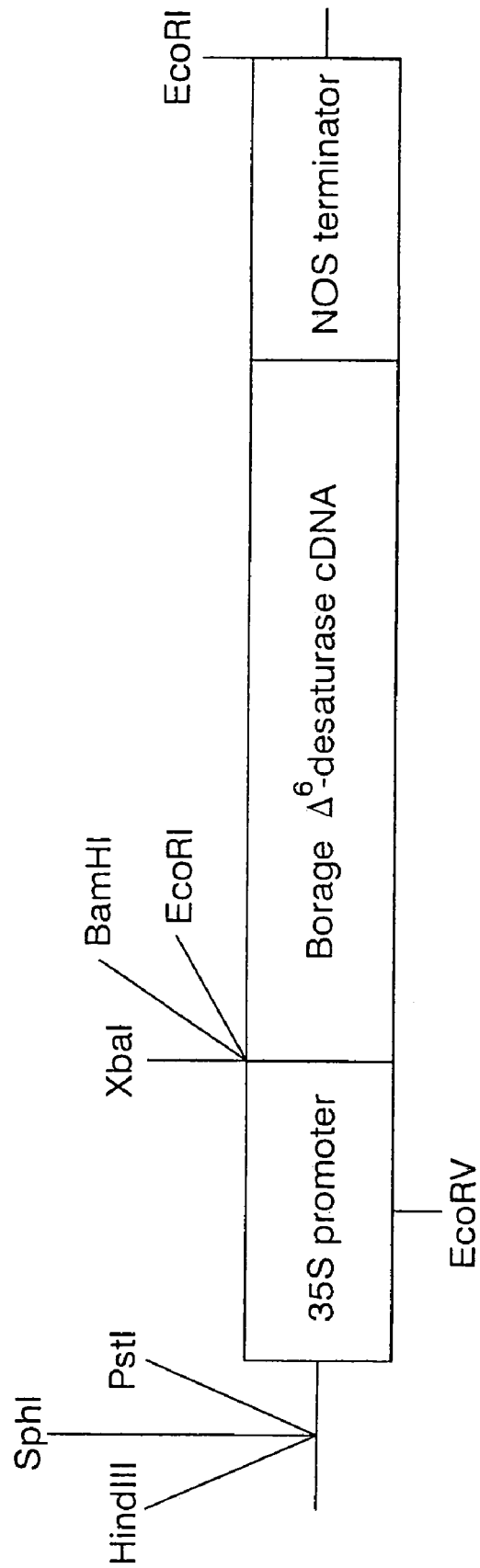
FIG. 7 is a restriction map of 221.Δ6.NOS and 121.Δ6.NOS. In 221.Δ6.NOS, the remaining portion of the plasmid is pBI221 and in 121.Δ6.NOS, the remaining portion of the plasmid is pBI121.

The vector pBI221 (Jefferson et al. 1987 EMBO J. 6:3901-3907) was prepared for ligation by digestion with BamHI and EcoICR I (Promega) which excises the GUS coding region leaving the 35S promoter and NOS terminator intact. The borage Δ6-desaturase cDNA was excised from the Bluescript plasmid (Stratagene) by digestion with BamHI and XhoI. The XhoI end was made blunt by use of the Klenow fragment. This fragment was then cloned into the BamHI/EcoICR I sites of pBI221, yielding 221.1Δ$^6$NOS (FIG. 7). In 221.1Δ$^6$.NOS, the remaining portion (backbone) of the restriction map depicted in FIG. 7 is pBI221.

EXAMPLE 11

Construction of 121.1Δ$^6$.NOS for Stable Transformation

The vector pBI121 (Jefferson et al. 1987 EMBO J. 6:3901-3907) was prepared for ligation by digestion with BamHI and EcoICR I (Promega) which excises the GUS coding region leaving the 35S promoter and NOS terminator intact. The borage Δ6-desaturase cDNA was excised from the Bluescript plasmid (Stratagene) by digestion with BamHI and XhoI. The XhoI end was made blunt by use of the Klenow fragment. This fragment was then cloned into the BamHI/EcoICR I sites of pBI121, yielding 121.1Δ$^6$NOS (FIG. 7). In 121.1Δ⁶.NOS, the remaining portion (backbone) of the restriction map depicted in FIG. 7 is pBI121.

EXAMPLE 12

Transient Expression

All work involving protoplasts was performed in a sterile hood. One ml of packed carrot suspension cells were digested in 30 mls plasmolyzing solution (25 g/l KCl, 3.5 g/l CaCl$_2$—H$_2$O, 10 mM MES, pH 5.6 and 0.2 M mannitol) with 1% cellulase, 0.1% pectolyase, and 0.1% dreisalase overnight, in the dark, at room temperature. Released protoplasts were filtered through a 150 μm mesh and pelleted by centrifugation (100×g, 5 min.) then washed twice in plasmolyzing solution. Protoplasts were counted using a double chambered hemocytometer. DNA was transfected into the protoplasts by PEG treatment as described by Nunberg and Thomas (1993 *Methods in Plant Molecular Biology and Biotechnology*, B. R. Glick and J. E. Thompson, eds. pp. 241-248) using 10⁶ protoplasts and 50-70 ug of plasmid DNA (221.Δ6.NOS). Protoplasts were cultured in 5 mls of MS media supplemented with 0.2M mannitol and 3 μm 2,4-D for 48 hours in the dark with shaking.

EXAMPLE 13

Stable Transformation of Tobacco 121.1Δ⁶NOS plasmid construction was used to transform tobacco (Nicotiana tabacum cv. xanthi) via *Agrobacterium* according to standard procedures (Horsh et al., 1985 Science 227: 1229-1231; Bogue et al., 1990 Mol. Gen. Genet. 221:49-57), except that initial transformants were selected on 100 ug/ml kanamycin.

EXAMPLE 14

Preparation and Analysis of Fatty Acid Methyl Esters (FAMEs)

Tissue from transfected protoplasts and transformed tobacco plants was frozen in liquid nitrogen and lyophilized overnight. FAMEs were prepared as described by Dahmer et al (1989 J. Amer. Oil Chem. Soc. 6:543-548). In some cases, the solvent was evaporated again, and the FAMEs were resuspended in ethyl acetate and extracted once with deionized water to remove any water soluble contaminants. The FAMEs were analyzed by gas chromatography (GC) on a J&W Scientific DB-wax column (30 m length, 0.25 mm ID, 0.25 μm film).

Figure 9A:
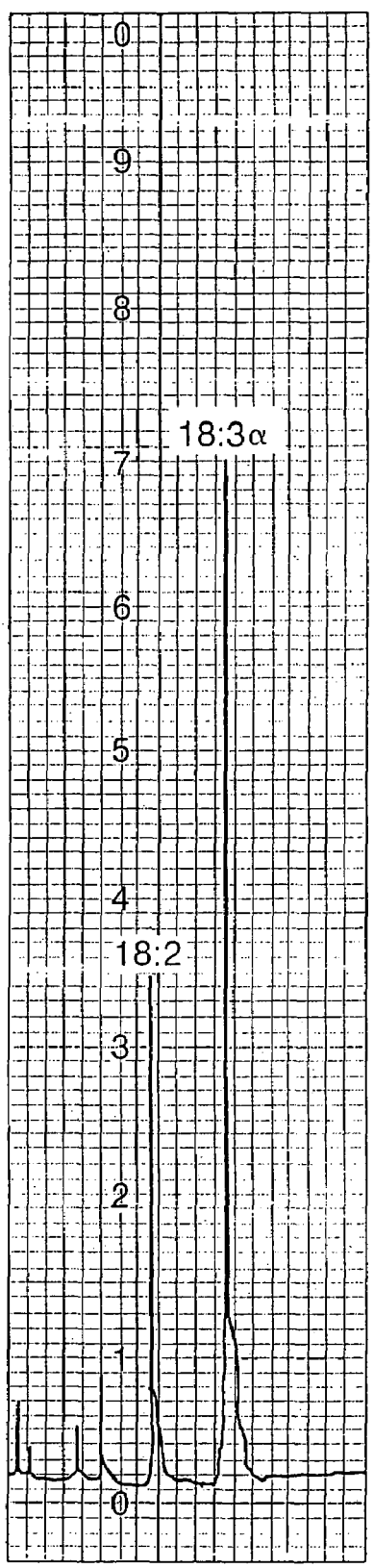
FIG. 9(A and B) provides gas liquid chromatography profiles of an untransformed tobacco leaf (FIG. 9A) and a tobacco leaf transformed with 121.Δ6.NOS (FIG. 9B). The positions of 18:2, 18:3 α, 18:3γ (GLA), and 18:4 are indicated.
Figure 9B:
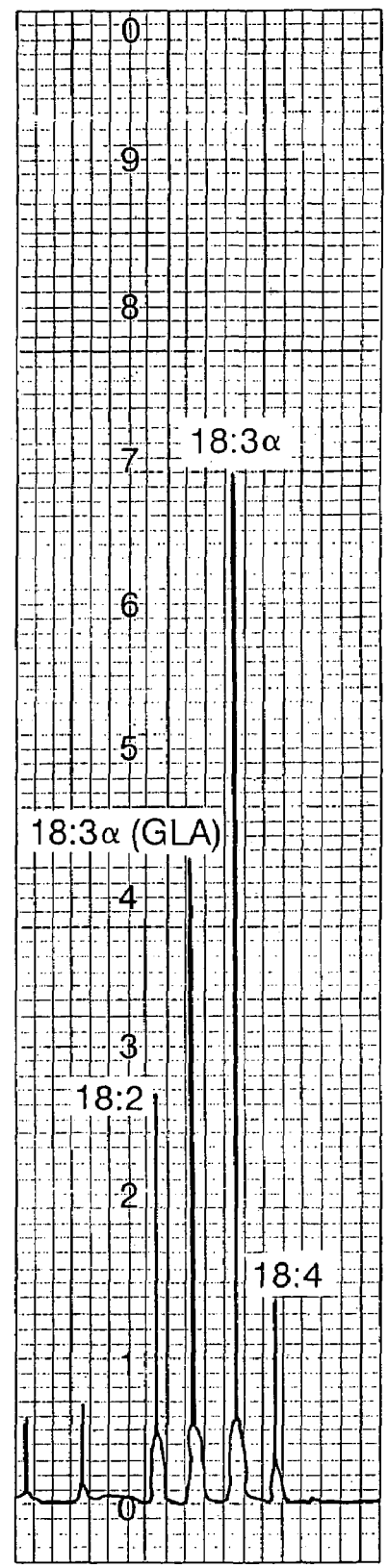

An example of a transient assay is shown in FIG. 8 which represents three independent transfections pooled together. The addition of the borage Δ6-desaturase cDNA corresponds with the appearance of gamma linolenic acid (GLA) which is one of the possible products of Δ6-desaturase. Furthermore, transgenic tobacco containing the borage Δ6-desaturase driven by the cauliflower mosaic virus 35S promoter also produce GLA as well as octa-decaenoic acid (18:4) which is formed by the further desaturation of GLA (FIG. 9). These results indicate that the borage delta 6-desaturase gene can be used to transform plant cells to achieve altered fatty acid compositions.

EXAMPLE 15

Isolation of an Evening Primrose Δ6-desaturase Gene

Total RNA was isolated from evening primrose embryos using the method of Chang, Puryear, and Cairney (1993) *Plant Mol Biol Reporter* 11:113-116. Poly A⁺ RNA was selected on oligotex beads (Qiagen) and used as a template for cDNA synthesis. The cDNA library was constructed in the lambda ZAP II vector (Stratagene) using the lambda ZAP II vector kit. The primary library was packaged with Gigapack II Gold packaging extract (Stratagene).

PCR primers based on sequences in the borage Δ6-desaturase gene were synthesized by a commercial source using standard protocols and included the following oligonucleotides:

```
5' AAACCAATCCATCCAAGRA 3'      SEQ ID NO:27

5' KTGGTGGAAATGGAMSCATAA 3'    SEQ ID NO:28
(R = A and G, K = G and T, M = A and C, S = G and
C)
```

A primer that matches a region that flanks the insertion site of the lambda ZAP II vector was also synthesized using an ABI394 DNA synthesizer and standard protocols. This primer ahd the following sequence:
5' TCTAGAACTAGTGGATC 3' SEQ ID NO:29

An aliquot of the cDNA library was used directly as template in a PCR reaction using SEQ ID NO: 27 and SEQ ID NO:29 as primers. The reactions were carried out in a volume of 50 μl using an annealing temperature of 50° C. for 2 minutes, an extension temperature of 72° C. for 1.5 minutes, and a melting temperature of 94° C. for 1 minute for 29 cycles. A final cycle with a 2 minute annealing at 50° C. and a 5 minute extension at 72° C. completed the reaction. One μl from this reaction was used as a template in a second reaction using the same conditions except that the primers were SEQ ID NO:27 and SEQ ID NO:28. A DNA fragment of predicted size based on the location of the primer sequences in the the borage Δ6-desaturase cDNA was isolated.

This PCR fragment was cloned into pT7 Blue (Novagen) and used to screen the evening primrose cDNA library at low stringency conditions: The hybridization buffer used was 1% bovine serum albumin (crystalline fraction V), 1 mM EDTA, 0.5 M NaHPO$_4$ pH7.2, and 7% SDS. The hybridizations were at 65° C. The wash buffer was 1 mM Na$_2$EDTA, 40 mM NaHPO$_4$pH7.2 and 1% SDS. Primary screens were washed at. 25° C. Secondary and tertiary screens were washed at 25° C., 37° C., and 42° C. One of the positively hybridizing clones that was identified in the evening primrose cDNA library was excised as a phagemid in pBluescript. The DNA sequence of the 1687 bp insert of this phagemid (pIB9748-4) was determined (FIG. 10, SEQ ID NO: 26) using the ABIPRISM™ dye terminator cycle sequencing core kit from Perkin Elmer according to the manufacturer's protocol. The sequence encodes a full length protein of 450 amino acids (SEQ ID NO:27) with a molecular weight of 51492 daltons.

Figure 11B:
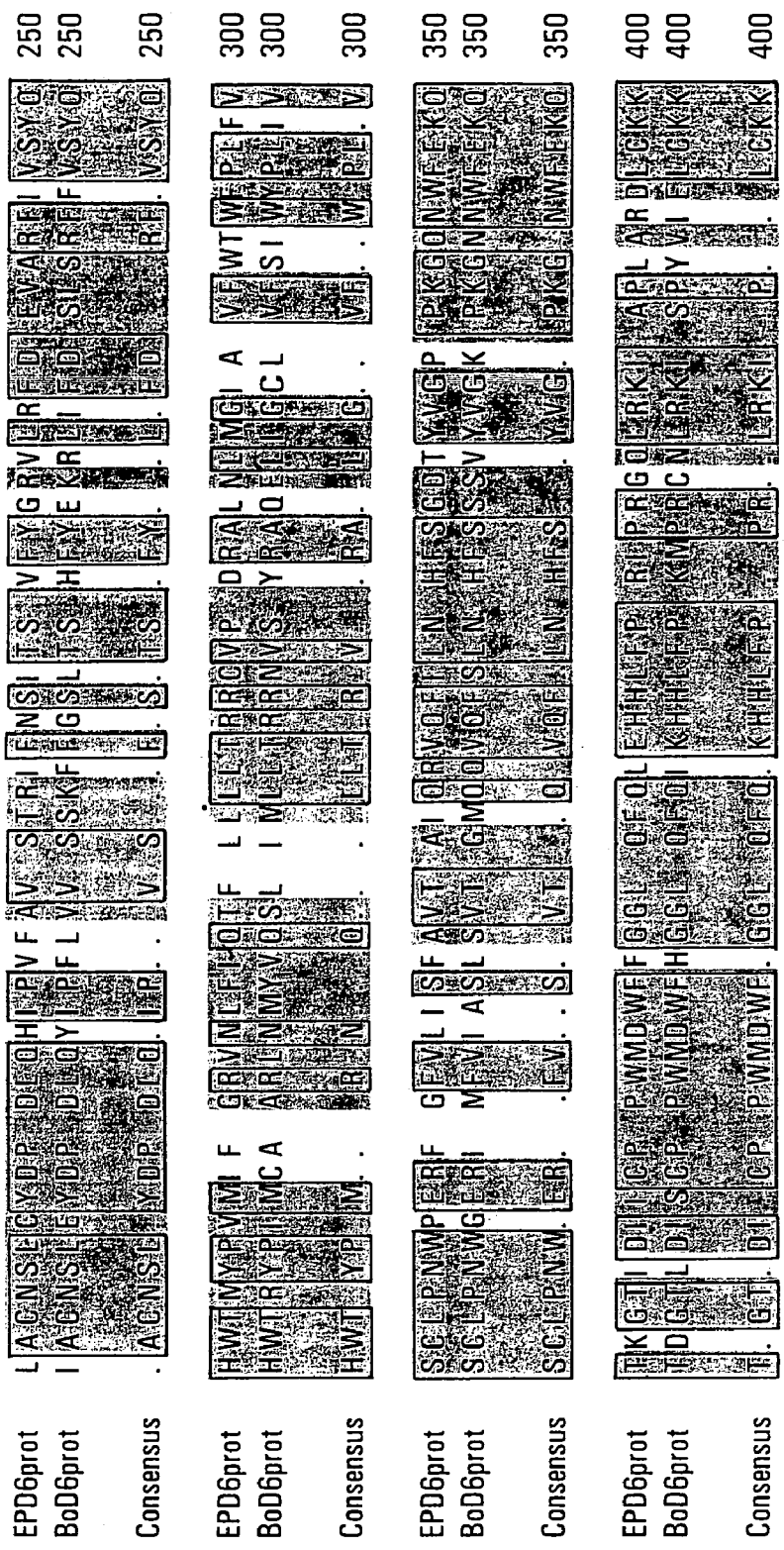
FIG. 11(A and C) provide formatted alignment of the evening primrose and borage Δ6-desaturase amino acid sequences.
Figure 11C:
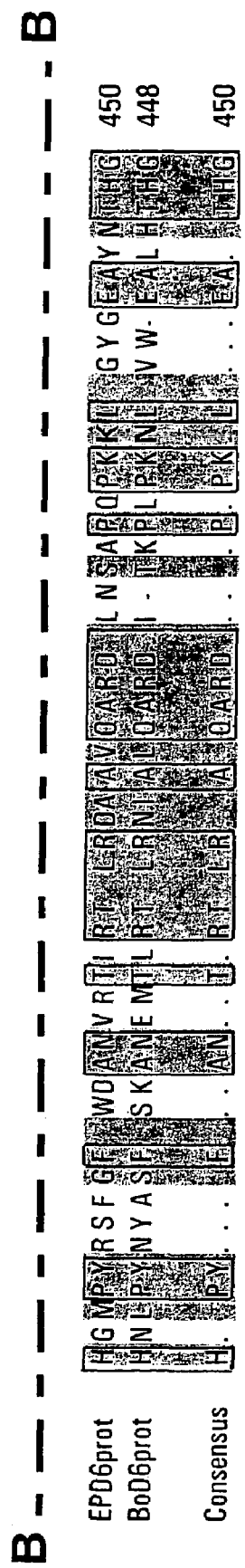
Figure 12A:
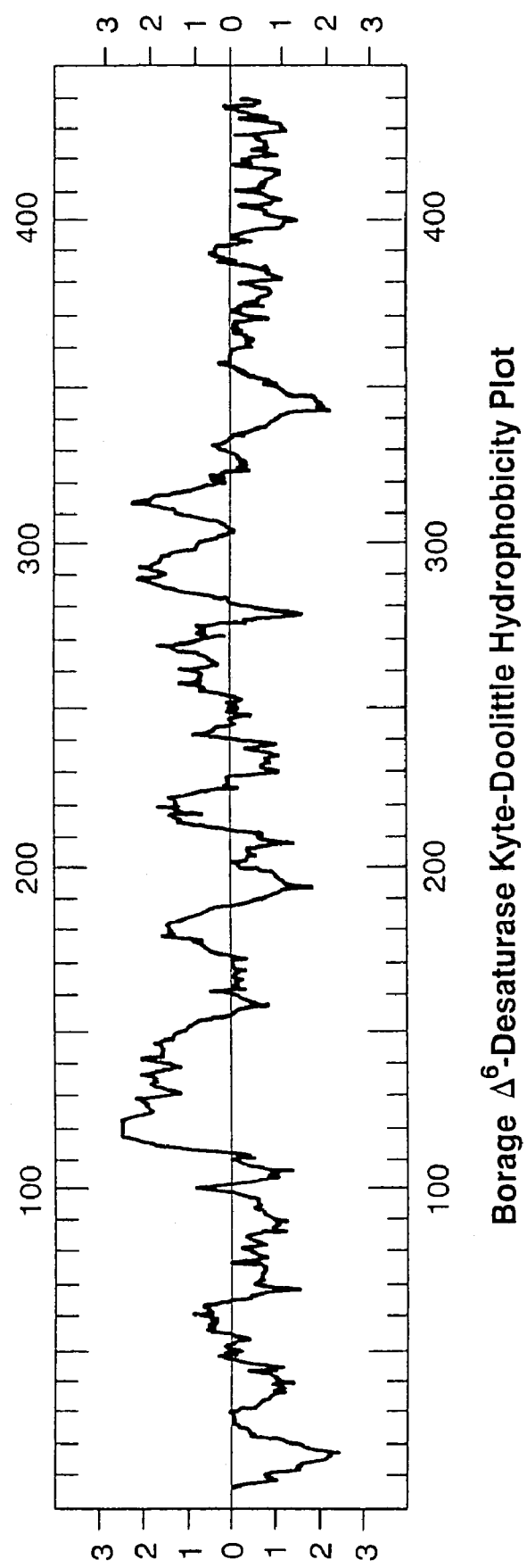
FIG. 12A is a Kyte-Doolittle hydrophobicity plot for borage Δ6-desaturase.
Figure 12B:
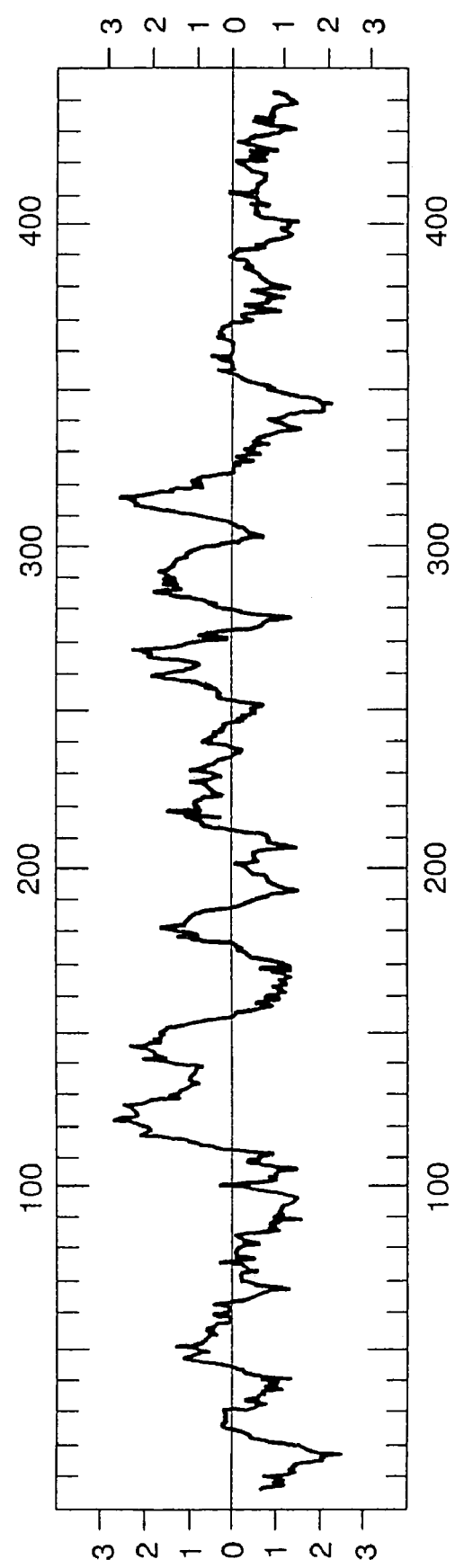
FIG. 12B is a Kyte-Doolittle hydrophobicity plot for evening primrose Δ6-desaturase.
Figure 13A:
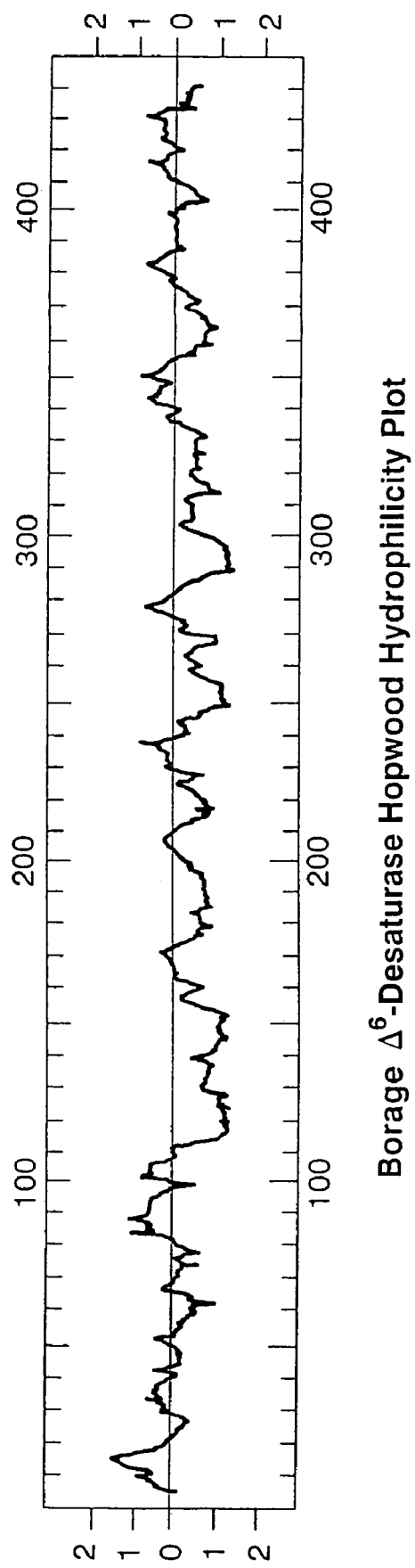
FIG. 13A is a Hopwood hydrophobicity plot for borage Δ6-desaturase. The y axis is a normalized parameter that estimates hydrophobicity; that the x axis represents the linear amino acid sequences.
Figure 13B:
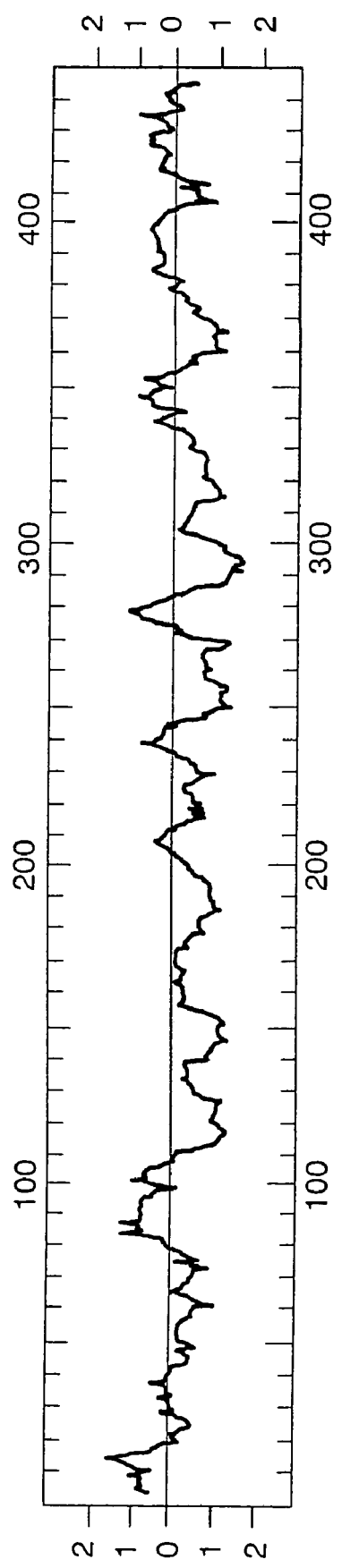
FIG. 13B is a Hopwood hydrophobicity plot for evening primrose Δ6-desaturase. X and y axes are as in FIG. 13A.
Figure 14A:
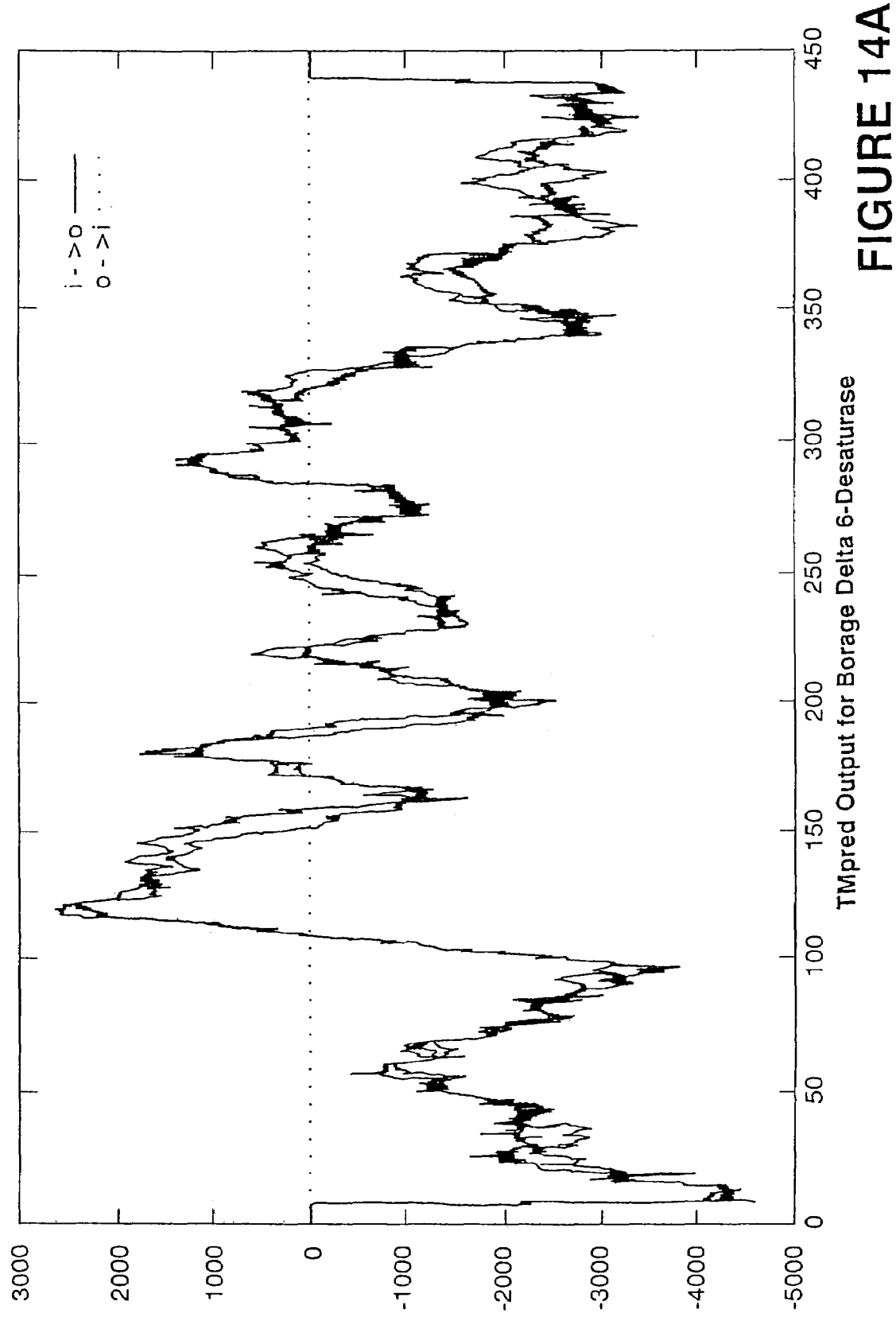
FIG. 14A graphically depicts the location of the transmembrane regions for borage Δ6-desaturase. Positive values (y-axis) greater than 500 are considered significant predictors of a membrane spanning region. The x-axis represents the linear amino acid sequences.
Figure 14B:
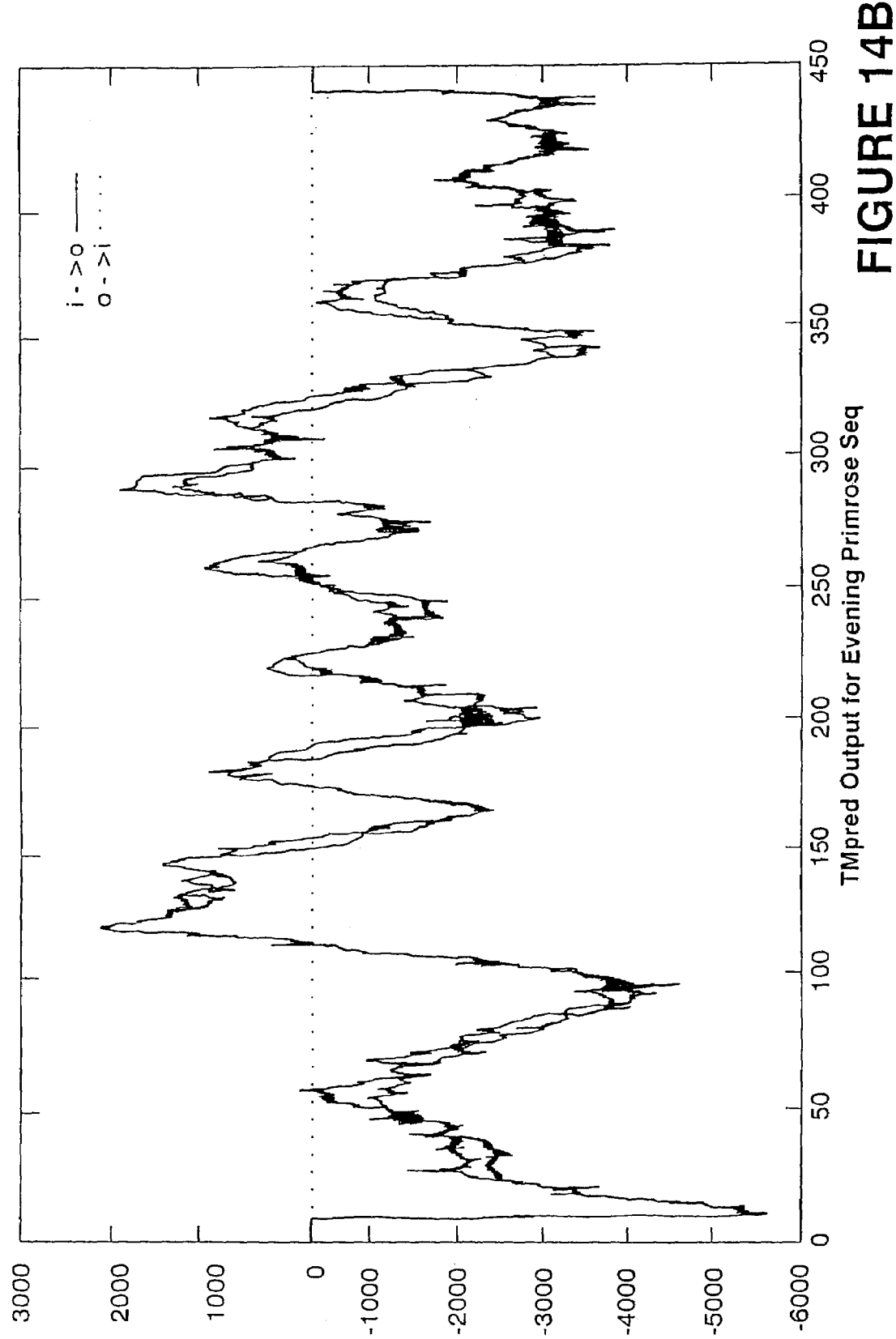
FIG. 14B graphically depicts the location of the transmembrane regions for evening primrose Δ6-desaturase. X and y axes are as in FIG. 14A.

Alignment of the deduced amino acid sequence with that of borage Δ6-desaturase was performed using the Geneworks program (FIG. 11). The evening primrose Δ6-desaturase protein is identical at 58% of the residues and similar at an additional 20% of the residues. Only two small gaps, near the carboxy terminal end of the protein were introduced by the program to obtain the alignment (FIG. 11). The two proteins were compared using two different alogorithms that measure the hydrophobicity of regions to the protein. FIGS. 12A and 12B are Kyte-Doolittle hydrophobicity plots of borage Δ6-desaturase and evening primrose Δ6-desaturase, respectively. FIGS. 13A and 13B are Hopwood hydrophobicity plots generated in the program DNA Strider for the same proteins. A discussion of the algorithim used to generate these plots can be found in Hopp, T. P. and Woods, K. R. 1983 *Molecular Immunology* 20:483-89. Substantial similarity exists between the borage and evening primrose proteins using either algorithm. TMPredict, a program that predicts the location of transmembrane regions of proteins was run on the two sequences and again similar results were obtained (FIGS. 14A and 14B). Several weights matrices are used in scoring the predictions as reported in Hofmann, K. and Stoffel, W. 1993 Biol. C. Hoppe-Scyler 347:156. Positive values (x-axis) greater than 500 are considered significant predictors of a membrane spanning region; the x-axis represents the linear amino acid sequences.

The membrane bound desaturases of plants possess three histidine rich motiffs (HRMs). These motiffs are identified in the evening primrose sequence and are indicated in FIG. 10 by underlined plain text. The motifs in this sequence were identical to those found in borage Δ6-desaturase with the exception of those that are italicized (S 161 and L374). The borage Δ6-desaturase is unique among known membrane bound desaturases in having a cytochrome b5 domain at the carboxy terminal end. The evening primrose protein encoded by pIB9748-4 also has this domain. The heme binding motiff of chtochrome b5 proteins is indicated in FIG. 10 by underlined bold text.

These data indicate that a Δ6-desaturase cDNA from evening primrose has been isolated and characterized.

EXAMPLE 16

Construction of Expression Vectors for Transient and Stable Expression of an Evening Primrose Δ6-desaturase The evening primrose Δ6-desaturase cDNA is excised from the Bluescript phagemid by digestion with Xba I and Xho I. The entire cDNA sequence including the 5' transcribed but untranslated region depicted in FIG. 10 (SEQ ID NO:26) is operably linked to any one of various promoters and/or other regulatory elements in an expression vector, in order to effect transcription and translation of the Δ6-desaturase gene. Alternatively, the cDNA sequence depicted in FIG. 10 may be trimmed at the 5' end so that the 5' transcribed but untranslated sequence is removed. The A of the ATG translational start codon is then made the first nucleotide following the promoter and/or other regulatory sequence in an expression vector.

In order to express the subject evening primrose cDNA in pBI221 (Jefferson et al. 1987 EMBO J. 6:3901-3907) the following manipulations are performed:

The plasmid pBI221 is digested with EcoICR I (Promega) or Ecl 136 II (NEB) and Xba I which excises the GUS coding region and leaves the 35S promoter and NOS terminator intact. The evening primrose Δ6-desaturase cDNA is excised from pIB9748-4 by digestion with Xba I and Xho I. The Xho I end is made blunt by use of the Klenow fragment. The excised gene is then cloned into the cloned into the Xba I/Eco ICR I sites of pBI221. The resulting construct is then transfected into carrot protoplasts. One ml of packed carrot suspension cells are digested in 30 ml of plasmolyzing solution (25 g/l KCl 3.5 g/l $CaCl_2$—$H_2O$, 10 mM MES, pH 5.6 and 0.2 M mannitol) with 1% cellulase 0.1% pectolyase, and 0.1% dreisalase overnight, in the dark, at room temperature. Released protoplasts are filtered through a 150 μm mesh and pelleted by centrifugation (100×g, 5 minutes), then washed twice in plasmolyzing solution. Protoplasts are counted using a double chambered hemocytometer. DNA is transfected into the protoplasts by PEG treatment as described by Nunberg and Thomas (1993 *Methods in Plant Molecular Biology and Biotechnology*, B. R. Glick and J. E. Thompson, eds. pp 241-248) using $10^6$ protoplasts and 50-70 ug of DNA from the above construct. Protoplasts are cultured in 5 ml of MS medium supplemented with 0.2 M mannitol and 3 μM 2, 4-D for 48 hours in the dark with shaking. Tobacco is transformed with the same Δ6-desaturase expression construct by following the method of Example 13.

In order to express the subject evening primrose cDNA in pBI121 (Jefferson et al. 1987 EMLBO J. 6:3901-3907), the following manipulations are performed:

The plasmid pBI121 is digested with EcoICR I (Promega) or Ecl 136 II (NEB) and Xba I which excises the GUS coding region and leaves the 35S promoter and NOS terminator intact. The evening primrose Δ6-desaturase cDNA is excised from pIB9748-4 by digestion with Xba I and Xho I. The Xho I end is made blunt by use of the Klenow fagment. The excised gene is then cloned into the Xba I/Eco ICR I sites of pBI121. The resulting construct is used to transform *Arabidopsis thaliana* via *Agrobacterium* according to standard protocols (Bechtold N., Ellis. J., and Pelletier, G 1993 C.R. Acad Sci Paris 316:1194-1199). Carrot and tobacco are transformed as described above.

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 3588 base pairs
      (B) TYPE: nucleic acid
      (C) STRANDEDNESS: both
      (D) TOPOLOGY: linear (ii) MOLECULE TYPE: DNA (genomic)

(ix) FEATURE:
    (A) NAME/KEY: CDS
    (B) LOCATION: 2002..3081

(xi) SEQUENCE DESCRIPTION: SEQ ID NO: 1:

```
GCTAGCCACC AGTGACGATG CCTTGAATTT GGCCATTCTG ACCCAGGCCC GTATTCTGAA    60
TCCCCGCATT CGCATTGTTA ATCGTTTGTT CAACCATGCC CTGGGTAAAC GTTTAGACAC   120
CACCTTGCCA GACCACGTTA GTTTGAGTGT TTCCGCCCTG GCGGCCCCGA TTTTTTCCTT   180
TGCGGCTTTG GGCAATCAGG CGATCGGGCA ATTGCGTTTG TTTGACCAGA CTTGGCCCAT   240
TCAGGAAATT GTCATTCACC AAGACCATCC CTGGCTCAAT TTACCCCTGG CGGATTTATG   300
GGATGATCCG AGCCGAATGT TGATCTATTA CCTACCGGCC CACAGTGAAA CGGATTTAGT   360
AGGCGCAGTG GTGAATAATT TAACGTTGCA ATCTGGGGAC CATTTAATAG TGGGACAAAA   420
ACCCCAACCC AAGACCAAAC GGCGATCGCC TTGGCGCAAA TTTTCCAAAC TGATTACCAA   480
CCTGCGGGAG TATCAGCGGT ATGTCCAACA GGTGATATGG GTGGTGTTGT TTTTATTGTT   540
GATGATTTTT CTGGCCACCT TCATCTACGT TTCCATTGAT CAACATATTG CCCCAGTGGA   600
CGCGTTGTAT TTTTCCGTGG GCATGATTAC CGGGGCCGGT GGCAAGGAAG AGGTGGCCGA   660
AAAGTCCCCC GATATCATCA AGTATTCAC AGTGGTGATG ATGATCGCCG GGCGGGGGT    720
GATTGGTATT TGTTATGCCC TACTGAATGA TTTCATCCTT GGCAGTCGCT TTAGTCAGTT   780
TTTGGATGCG GCCAAGTTAC CCGATCGCCA TCACATCATC ATTTGTGGGC TGGGGGGAGT   840
GAGCATGGCC ATTATTGAAG AGTTAATTCA CCAGGGCCAT GAAATTGTGG TAATCGAAAA   900
GGATACAGAT AATCGTTTCT TGCATACGGC CCGCTCCCTG GGGGTGCCCG TAATTGTGGA   960
GGATGCCCGC CTAGAAAGAA CGTTGGCCTG CGCCAATATC AACCGAGCCG AAGCCATTGT  1020
GGTGGCCACC AGCGACGACA CCGTTAACTT GGAAATTGGC CTAACTGCCA AGGCGATCGC  1080
CCCTAGCCTG CCAGTGGTGT TGCGTTGCCA GGATGCCCAG TTTAGCCTGT CCCTGCAGGA  1140
AGTATTTGAA TTTGAAACGG TGCTTTGTCC GGCGGAATTG GCCACCTATT CCTTTGCGGC  1200
GGCGGCCCTG GGGGGCAAAA TTTTGGGCAA CGGCATGACC GATGATTTGC TGTGGGTAGC  1260
CCTAGCCACC TTAATCACTC CTAACCATCC CTTTGCCGAC CAATTGGTTA AAATTGCAGC  1320
CCAAAAGTCT GATTTCGTTC CCCTCTATCT AGAACGGGGT GGCAAAACCA TCCATAGCTG  1380
GGAATTATTG GTACCCATC TCGACTCTGG AGACGTGTTG TATTTAACCA TGCCCGCCAC  1440
TGCCCTAGAG CAACTTTGGC GATCGCCCCG TGCCACTGCT GATCCTCTGG ACTCTTTTTT  1500
GGTTTAGCAT GGGGGGATGG AACTCTTGAC TCGGCCCAAT GGTGATCAAG AAAGAACGCT  1560
TTGTCTATGT TTAGTATTTT TAAGTTAACC AACAGCAGAG GATAACTTCC AAAAGAAATT  1620
AAGCTCAAAA AGTAGCAAAA TAAGTTTAAT TCATAACTGA GTTTTACTGC TAAACAGCGG  1680
TGCAAAAAAG TCAGATAAAA TAAAAGCTTC ACTTCGGTTT TATATTGTGA CCATGGTTCC  1740
CAGGCATCTG CTCTAGGGAG TTTTTCCGCT GCCTTTAGAG AGTATTTTCT CCAAGTCGGC  1800
TAACTCCCCC ATTTTTAGGC AAAATCATAT ACAGACTATC CCAATATTGC CAGAGCTTTG  1860
ATGACTCACT GTAGAAGGCA GACTAAAATT CTAGCAATGG ACTCCCAGTT GGAATAAATT  1920
TTAGTCTCC CCCGGCGCTG GAGTTTTTTT GTAGTTAATG GCGGTATAAT GTGAAAGTTT  1980
TTTATCTATT TAAATTTATA A ATG CTA ACA GCG GAA AGA ATT AAA TTT ACC   2031
                       Met Leu Thr Ala Glu Arg Ile Lys Phe Thr
                        1               5                  10

CAG AAA CGG GGG TTT CGT CGG GTA CTA AAC CAA CGG GTG GAT GCC TAC   2079
```

-continued

```
        Gln Lys Arg Gly Phe Arg Arg Val Leu Asn Gln Arg Val Asp Ala Tyr
                        15                  20                  25

TTT GCC GAG CAT GGC CTG ACC CAA AGG GAT AAT CCC TCC ATG TAT CTG         2127
Phe Ala Glu His Gly Leu Thr Gln Arg Asp Asn Pro Ser Met Tyr Leu
                30                  35                  40

AAA ACC CTG ATT ATT GTG CTC TGG TTG TTT TCC GCT TGG GCC TTT GTG         2175
Lys Thr Leu Ile Ile Val Leu Trp Leu Phe Ser Ala Trp Ala Phe Val
            45                  50                  55

CTT TTT GCT CCA GTT ATT TTT CCG GTG CGC CTA CTG GGT TGT ATG GTT         2223
Leu Phe Ala Pro Val Ile Phe Pro Val Arg Leu Leu Gly Cys Met Val
        60                  65                  70

TTG GCG ATC GCC TTG GCG GCC TTT TCC TTC AAT GTC GGC CAC GAT GCC         2271
Leu Ala Ile Ala Leu Ala Ala Phe Ser Phe Asn Val Gly His Asp Ala
    75                  80                  85                  90

AAC CAC AAT GCC TAT TCC TCC AAT CCC CAC ATC AAC CGG GTT CTG GGC         2319
Asn His Asn Ala Tyr Ser Ser Asn Pro His Ile Asn Arg Val Leu Gly
                95                  100                 105

ATG ACC TAC GAT TTT GTC GGG TTA TCT AGT TTT CTT TGG CGC TAT CGC         2367
Met Thr Tyr Asp Phe Val Gly Leu Ser Ser Phe Leu Trp Arg Tyr Arg
                110                 115                 120

CAC AAC TAT TTG CAC CAC ACC TAC ACC AAT ATT CTT GGC CAT GAC GTG         2415
His Asn Tyr Leu His His Thr Tyr Thr Asn Ile Leu Gly His Asp Val
            125                 130                 135

GAA ATC CAT GGA GAT GGC GCA GTA CGT ATG AGT CCT GAA CAA GAA CAT         2463
Glu Ile His Gly Asp Gly Ala Val Arg Met Ser Pro Glu Gln Glu His
        140                 145                 150

GTT GGT ATT TAT CGT TTC CAG CAA TTT TAT ATT TGG GGT TTA TAT CTT         2511
Val Gly Ile Tyr Arg Phe Gln Gln Phe Tyr Ile Trp Gly Leu Tyr Leu
155                 160                 165                 170

TTC ATT CCC TTT TAT TGG TTT CTC TAC GAT GTC TAC CTA GTG CTT AAT         2559
Phe Ile Pro Phe Tyr Trp Phe Leu Tyr Asp Val Tyr Leu Val Leu Asn
                175                 180                 185

AAA GGC AAA TAT CAC GAC CAT AAA ATT CCT CCT TTC CAG CCC CTA GAA         2607
Lys Gly Lys Tyr His Asp His Lys Ile Pro Pro Phe Gln Pro Leu Glu
                190                 195                 200

TTA GCT AGT TTG CTA GGG ATT AAG CTA TTA TGG CTC GGC TAC GTT TTC         2655
Leu Ala Ser Leu Leu Gly Ile Lys Leu Leu Trp Leu Gly Tyr Val Phe
            205                 210                 215

GGC TTA CCT CTG GCT CTG GGC TTT TCC ATT CCT GAA GTA TTA ATT GGT         2703
Gly Leu Pro Leu Ala Leu Gly Phe Ser Ile Pro Glu Val Leu Ile Gly
        220                 225                 230

GCT TCG GTA ACC TAT ATG ACC TAT GGC ATC GTG GTT TGC ACC ATC TTT         2751
Ala Ser Val Thr Tyr Met Thr Tyr Gly Ile Val Val Cys Thr Ile Phe
235                 240                 245                 250

ATG CTG GCC CAT GTG TTG GAA TCA ACT GAA TTT CTC ACC CCC GAT GGT         2799
Met Leu Ala His Val Leu Glu Ser Thr Glu Phe Leu Thr Pro Asp Gly
                255                 260                 265

GAA TCC GGT GCC ATT GAT GAC GAG TGG GCT ATT TGC CAA ATT CGT ACC         2847
Glu Ser Gly Ala Ile Asp Asp Glu Trp Ala Ile Cys Gln Ile Arg Thr
                270                 275                 280

ACG GCC AAT TTT GCC ACC AAT AAT CCC TTT TGG AAC TGG TTT TGT GGC         2895
Thr Ala Asn Phe Ala Thr Asn Asn Pro Phe Trp Asn Trp Phe Cys Gly
            285                 290                 295

GGT TTA AAT CAC CAA GTT ACC CAC CAT CTT TTC CCC AAT ATT TGT CAT         2943
Gly Leu Asn His Gln Val Thr His His Leu Phe Pro Asn Ile Cys His
        300                 305                 310

ATT CAC TAT CCC CAA TTG GAA AAT ATT ATT AAG GAT GTT TGC CAA GAG         2991
Ile His Tyr Pro Gln Leu Glu Asn Ile Ile Lys Asp Val Cys Gln Glu
315                 320                 325                 330
```

-continued

```
TTT GGT GTG GAA TAT AAA GTT TAT CCC ACC TTC AAA GCG GCG ATC GCC        3039
Phe Gly Val Glu Tyr Lys Val Tyr Pro Thr Phe Lys Ala Ala Ile Ala
                335                 340                 345

TCT AAC TAT CGC TGG CTA GAG GCC ATG GGC AAA GCA TCG TGACATTGCC         3088
Ser Asn Tyr Arg Trp Leu Glu Ala Met Gly Lys Ala Ser
            350                 355

TTGGGATTGA AGCAAAATGG CAAAATCCCT CGTAAATCTA TGATCGAAGC CTTTCTGTTG      3148

CCCGCCGACC AAATCCCCGA TGCTGACCAA AGGTTGATGT TGGCATTGCT CCAAACCCAC      3208

TTTGAGGGGG TTCATTGGCC GCAGTTTCAA GCTGACCTAG GAGGCAAAGA TTGGGTGATT      3268

TTGCTCAAAT CCGCTGGGAT ATTGAAAGGC TTCACCACCT TTGGTTTCTA CCCTGCTCAA      3328

TGGGAAGGAC AAACCGTCAG AATTGTTTAT TCTGGTGACA CCATCACCGA CCCATCCATG      3388

TGGTCTAACC CAGCCCTGGC CAAGGCTTGG ACCAAGGCCA TGCAAATTCT CCACGAGGCT      3448

AGGCCAGAAA AATTATATTG GCTCCTGATT TCTTCCGGCT ATCGCACCTA CCGATTTTTG      3508

AGCATTTTTG CCAAGGAATT CTATCCCCAC TATCTCCATC CCACTCCCCC GCCTGTACAA      3568

AATTTTATCC ATCAGCTAGC                                                  3588
```

(2) INFORMATION FOR SEQ ID NO: 2:

(i) SEQUENCE CHARACTERISTICS:
        (A) LENGTH: 359 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Leu Thr Ala Glu Arg Ile Lys Phe Thr Gln Lys Arg Gly Phe Arg
 1               5                  10                  15

Arg Val Leu Asn Gln Arg Val Asp Ala Tyr Phe Ala Glu His Gly Leu
                20                  25                  30

Thr Gln Arg Asp Asn Pro Ser Met Tyr Leu Lys Thr Leu Ile Ile Val
            35                  40                  45

Leu Trp Leu Phe Ser Ala Trp Ala Phe Val Leu Phe Ala Pro Val Ile
     50                  55                  60

Phe Pro Val Arg Leu Leu Gly Cys Met Val Leu Ala Ile Ala Leu Ala
65                  70                  75                  80

Ala Phe Ser Phe Asn Val Gly His Asp Ala Asn His Asn Ala Tyr Ser
                85                  90                  95

Ser Asn Pro His Ile Asn Arg Val Leu Gly Met Thr Tyr Asp Phe Val
            100                 105                 110

Gly Leu Ser Ser Phe Leu Trp Arg Tyr Arg His Asn Tyr Leu His His
        115                 120                 125

Thr Tyr Thr Asn Ile Leu Gly His Asp Val Glu Ile His Gly Asp Gly
    130                 135                 140

Ala Val Arg Met Ser Pro Glu Gln Glu His Val Gly Ile Tyr Arg Phe
145                 150                 155                 160

Gln Gln Phe Tyr Ile Trp Gly Leu Tyr Leu Phe Ile Pro Phe Tyr Trp
                165                 170                 175

Phe Leu Tyr Asp Val Tyr Leu Val Leu Asn Lys Gly Lys Tyr His Asp
            180                 185                 190

His Lys Ile Pro Pro Phe Gln Pro Leu Glu Leu Ala Ser Leu Leu Gly
        195                 200                 205

Ile Lys Leu Leu Trp Leu Gly Tyr Val Phe Gly Leu Pro Leu Ala Leu
    210                 215                 220
```

```
Gly Phe Ser Ile Pro Glu Val Leu Ile Gly Ala Ser Val Thr Tyr Met
225                 230                 235                 240

Thr Tyr Gly Ile Val Val Cys Thr Ile Phe Met Leu Ala His Val Leu
                245                 250                 255

Glu Ser Thr Glu Phe Leu Thr Pro Asp Gly Glu Ser Gly Ala Ile Asp
                260                 265                 270

Asp Glu Trp Ala Ile Cys Gln Ile Arg Thr Thr Ala Asn Phe Ala Thr
            275                 280                 285

Asn Asn Pro Phe Trp Asn Trp Phe Cys Gly Gly Leu Asn His Gln Val
        290                 295                 300

Thr His His Leu Phe Pro Asn Ile Cys His Ile His Tyr Pro Gln Leu
305                 310                 315                 320

Glu Asn Ile Ile Lys Asp Val Cys Gln Glu Phe Gly Val Glu Tyr Lys
                325                 330                 335

Val Tyr Pro Thr Phe Lys Ala Ala Ile Ala Ser Asn Tyr Arg Trp Leu
            340                 345                 350

Glu Ala Met Gly Lys Ala Ser
            355

(2) INFORMATION FOR SEQ ID NO: 3:

(i) SEQUENCE CHARACTERISTICS:
        (A) LENGTH: 1884 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO: 3:

AGCTTCACTT CGGTTTTATA TTGTGACCAT GGTTCCCAGG CATCTGCTCT AGGGAGTTTT      60

TCCGCTGCCT TTAGAGAGTA TTTTCTCCAA GTCGGCTAAC TCCCCCATTT TTAGGCAAAA     120

TCATATACAG ACTATCCCAA TATTGCCAGA GCTTTGATGA CTCACTGTAG AAGGCAGACT     180

AAAATTCTAG CAATGGACTC CCAGTTGGAA TAAATTTTTA GTCTCCCCCG GCGCTGGAGT     240

TTTTTTGTAG TTAATGGCGG TATAATGTGA AAGTTTTTTA TCTATTTAAA TTTATAAATG     300

CTAACAGCGG AAAGAATTAA ATTTACCCAG AAACGGGGGT TTCGTCGGGT ACTAAACCAA     360

CGGGTGGATG CCTACTTTGC CGAGCATGGC CTGACCCAAA GGGATAATCC CTCCATGTAT     420

CTGAAAACCC TGATTATTGT GCTCTGGTTG TTTTCCGCTT GGGCCTTTGT GCTTTTTGCT     480

CCAGTTATTT TTCCGGTGCG CCTACTGGGT TGTATGGTTT TGGCGATCGC CTTGGCGGCC     540

TTTTCCTTCA ATGTCGGCCA CGATGCCAAC ACAATGCCT ATTCCTCCAA TCCCCACATC     600

AACCGGGTTC TGGGCATGAC CTACGATTTT GTCGGGTTAT CTAGTTTTCT TTGGCGCTAT     660

CGCCACAACT ATTTGCACCA CACCTACACC AATATTCTTG CCATGACGT GGAAATCCAT     720

GGAGATGGCG CAGTACGTAT GAGTCCTGAA CAAGAACATG TTGGTATTTA TCGTTTCCAG     780

CAATTTTATA TTTGGGGTTT ATATCTTTTC ATTCCCTTTT ATTGGTTTCT CTACGATGTC     840

TACCTAGTGC TTAATAAAGG CAAATATCAC GACCATAAAA TTCCTCCTTT CCAGCCCCTA     900

GAATTAGCTA GTTTGCTAGG GATTAAGCTA TTATGGCTCG GCTACGTTTT CGGCTTACCT     960

CTGGCTCTGG GCTTTTCCAT TCCTGAAGTA TTAATTGGTG CTTCGGTAAC CTATATGACC    1020

TATGGCATCG TGGTTTGCAC CATCTTTATG CTGGCCCATG TGTTGGAATC AACTGAATTT    1080

CTCACCCCCG ATGGTGAATC CGGTGCCATT GATGACGAGT GGGCTATTTG CCAAATTCGT    1140
```

-continued

| | |
|---|---|
| ACCACGGCCA ATTTTGCCAC CAATAATCCC TTTTGGAACT GGTTTTGTGG CGGTTTAAAT | 1200 |
| CACCAAGTTA CCCACCATCT TTTCCCCAAT ATTTGTCATA TTCACTATCC CCAATTGGAA | 1260 |
| AATATTATTA AGGATGTTTG CCAAGAGTTT GGTGTGGAAT ATAAAGTTTA TCCCACCTTC | 1320 |
| AAAGCGGCGA TCGCCTCTAA CTATCGCTGG CTAGAGGCCA TGGGCAAAGC ATCGTGACAT | 1380 |
| TGCCTTGGGA TTGAAGCAAA ATGGCAAAAT CCCTCGTAAA TCTATGATCG AAGCCTTTCT | 1440 |
| GTTGCCCGCC GACCAAATCC CCGATGCTGA CCAAAGGTTG ATGTTGGCAT TGCTCCAAAC | 1500 |
| CCACTTTGAG GGGGTTCATT GGCCGCAGTT TCAAGCTGAC CTAGGAGGCA AGATTGGGT | 1560 |
| GATTTTGCTC AAATCCGCTG GGATATTGAA AGGCTTCACC ACCTTTGGTT TCTACCCTGC | 1620 |
| TCAATGGGAA GGACAAACCG TCAGAATTGT TTATTCTGGT GACACCATCA CCGACCCATC | 1680 |
| CATGTGGTCT AACCCAGCCC TGGCCAAGGC TTGGACCAAG GCCATGCAAA TTCTCCACGA | 1740 |
| GGCTAGGCCA GAAAAATTAT ATTGGCTCCT GATTTCTTCC GGCTATCGCA CCTACCGATT | 1800 |
| TTTGAGCATT TTTGCCAAGG AATTCTATCC CCACTATCTC CATCCCACTC CCCCGCCTGT | 1860 |
| ACAAAATTTT ATCCATCAGC TAGC | 1884 |

(2) INFORMATION FOR SEQ ID NO: 4:

(i) SEQUENCE CHARACTERISTICS:
        (A) LENGTH: 1685 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO: 4:

| | |
|---|---|
| AATATCTGCC TACCCTCCCA AAGAGAGTAG TCATTTTTCA TCAATGGCTG CTCAAATCAA | 60 |
| GAAATACATT ACCTCAGATG AACTCAAGAA CCACGATAAA CCCGGAGATC TATGGATCTC | 120 |
| GATTCAAGGG AAAGCCTATG ATGTTTCGGA TTGGGTGAAA GACCATCCAG GTGGCAGCTT | 180 |
| TCCCTTGAAG AGTCTTGCTG GTCAAGAGGT AACTGATGCA TTTGTTGCAT TCCATCCTGC | 240 |
| CTCTACATGG AAGAATCTTG ATAAGTTTTT CACTGGGTAT TATCTTAAAG ATTACTCTGT | 300 |
| TTCTGAGGTT TCTAAAGATT ATAGGAAGCT TGTGTTTGAG TTTTCTAAAA TGGGTTTGTA | 360 |
| TGACAAAAAA GGTCATATTA TGTTTGCAAC TTTGTGCTTT ATAGCAATGC TGTTTGCTAT | 420 |
| GAGTGTTTAT GGGGTTTTGT TTTGTGAGGG TGTTTTGGTA CATTTGTTTT CTGGGTGTTT | 480 |
| GATGGGGTTT CTTTGGATTC AGAGTGGTTG GATTGGACAT GATGCTGGGC ATTATATGGT | 540 |
| AGTGTCTGAT TCAAGGCTTA ATAAGTTTAT GGGTATTTTT GCTGCAAATT GTCTTTCAGG | 600 |
| AATAAGTATT GGTTGGTGGA AATGGAACCA TAATGCACAT CACATTGCCT GTAATAGCCT | 660 |
| TGAATATGAC CCTGATTTAC AATATATACC ATTCCTTGTT GTGTCTTCCA AGTTTTTTGG | 720 |
| TTCACTCACC TCTCATTTCT ATGAGAAAAG GTTGACTTTT GACTCTTTAT CAAGATTCTT | 780 |
| TGTAAGTTAT CAACATTGGA CATTTTACCC TATTATGTGT GCTGCTAGGC TCAATATGTA | 840 |
| TGTACAATCT CTCATAATGT TGTTGACCAA GAGAAATGTG TCCTATCGAG CTCAGGAACT | 900 |
| CTTGGGATGC CTAGTGTTCT CGATTTGGTA CCCGTTGCTT GTTTCTTGTT TGCCTAATTG | 960 |
| GGGTGAAAGA ATTATGTTTG TTATTGCAAG TTTATCAGTG ACTGGAATGC AACAAGTTCA | 1020 |
| GTTCTCCTTG AACCACTTCT CTTCAAGTGT TTATGTTGGA AAGCCTAAAG GGAATAATTG | 1080 |
| GTTTGAGAAA CAAACGGATG GGACACTTGA CATTTCTTGT CCTCCTTGGA TGGATTGGTT | 1140 |
| TCATGGTGGA TTGCAATTCC AAATTGAGCA TCATTTGTTT CCCAAGATGC CTAGATGCAA | 1200 |

-continued

```
CCTTAGGAAA ATCTCGCCCT ACGTGATCGA GTTATGCAAG AAACATAATT TGCCTTACAA    1260

TTATGCATCT TTCTCCAAGG CCAATGAAAT GACACTCAGA ACATTGAGGA ACACAGCATT    1320

GCAGGCTAGG GATATAACCA AGCCGCTCCC GAAGAATTTG GTATGGGAAG CTCTTCACAC    1380

TCATGGTTAA AATTACCCTT AGTTCATGTA ATAATTTGAG ATTATGTATC TCCTATGTTT    1440

GTGTCTTGTC TTGGTTCTAC TTGTTGGAGT CATTGCAACT TGTCTTTTAT GGTTTATTAG    1500

ATGTTTTTTA ATATATTTTA GAGGTTTTGC TTTCATCTCC ATTATTGATG AATAAGGAGT    1560

TGCATATTGT CAATTGTTGT GCTCAATATC TGATATTTTG GAATGTACTT TGTACCACTG    1620

TGTTTTCAGT TGAAGCTCAT GTGTACTTCT ATAGACTTTG TTTAAATGGT TATGTCATGT    1680

TATTT                                                                1685
```

(2) INFORMATION FOR SEQ ID NO: 5:

(i) SEQUENCE CHARACTERISTICS:
        (A) LENGTH: 448 amino acids
        (B) TYPE: amino acid
        (D) TOPOLOGY: linear (ii) MOLECULE TYPE: Protein (xi) SEQUENCE DESCRIPTION: SEQ ID NO: 5:

```
Met Ala Ala Gln Ile Lys Lys Tyr Ile Thr Ser Asp Glu Leu Lys Asn
 1               5                  10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
 50                  55                  60

Pro Ala Ser Thr Trp Lys Asn Leu Asp Lys Phe Phe Thr Gly Tyr Tyr
 65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
```

```
                    260                 265                 270
Leu Leu Thr Lys Arg Asn Val Ser Tyr Arg Ala Gln Glu Leu Leu Gly
            275                 280                 285
Cys Leu Val Phe Ser Ile Trp Tyr Pro Leu Leu Val Ser Cys Leu Pro
            290                 295                 300
Asn Trp Gly Glu Arg Ile Met Phe Val Ile Ala Ser Leu Ser Val Thr
305                 310                 315                 320
Gly Met Gln Gln Val Gln Phe Ser Leu Asn His Phe Ser Ser Val
                325                 330                 335
Tyr Val Gly Lys Pro Lys Gly Asn Asn Trp Phe Glu Lys Gln Thr Asp
            340                 345                 350
Gly Thr Leu Asp Ile Ser Cys Pro Pro Trp Met Asp Trp Phe His Gly
            355                 360                 365
Gly Ser Gln Phe Gln Ile Glu His His Leu Phe Pro Lys Met Pro Arg
            370                 375                 380
Cys Asn Leu Arg Lys Ile Ser Pro Tyr Val Ile Glu Leu Cys Lys Lys
385                 390                 395                 400
His Asn Leu Pro Tyr Asn Tyr Ala Ser Phe Ser Lys Ala Asn Glu Met
                405                 410                 415
Thr Leu Arg Thr Leu Arg Asn Thr Ala Leu Gln Ala Arg Asp Ile Thr
            420                 425                 430
Lys Pro Leu Pro Lys Asn Leu Val Trp Glu Ala Leu His Thr His Gly
            435                 440                 445
```

(2) INFORMATION FOR SEQ ID NO: 6:

(i) SEQUENCE CHARACTERISTICS:
        (A) LENGTH: 8 amino acids
        (B) TYPE: amino acid
        (D) TOPOLOGY: linear (ii) MOLECULE TYPE: Peptide (xi) SEQUENCE DESCRIPTION: SEQ ID NO: 6:

```
Trp Ile Gly His Asp Ala Gly His
1               5
```

(2) INFORMATION FOR SEQ ID NO: 7:

(i) SEQUENCE CHARACTERISTICS:
        (A) LENGTH: 8 amino acids
        (B) TYPE: amino acid
        (D) TOPOLOGY: linear (ii) MOLECULE TYPE: Peptide (xi) SEQUENCE DESCRIPTION: SEQ ID NO: 7:

```
Asn Val Gly His Asp Ala Asn His
1               5
```

(2) INFORMATION FOR SEQ ID NO: 8:

(i) SEQUENCE CHARACTERISTICS:
        (A) LENGTH: 8 amino acids
        (B) TYPE: amino acid
        (D) TOPOLOGY: linear (ii) MOLECULE TYPE: Peptide (xi) SEQUENCE DESCRIPTION: SEQ ID NO: 8:

```
Val Leu Gly His Asp Cys Gly His
1               5
```

(2) INFORMATION FOR SEQ ID NO: 9:

(i) SEQUENCE CHARACTERISTICS:
        (A) LENGTH: 8 amino acids
        (B) TYPE: amino acid
        (D) TOPOLOGY: linear (ii) MOLECULE TYPE: DNA (peptide)

(xi) SEQUENCE DESCRIPTION: SEQ ID NO: 9:

```
Val Ile Ala His Glu Cys Gly His
1               5
```

(2) INFORMATION FOR SEQ ID NO: 10:

(i) SEQUENCE CHARACTERISTICS:
        (A) LENGTH: 8 amino acids
        (B) TYPE: amino acid
        (D) TOPOLOGY: linear (ii) MOLECULE TYPE: Peptide (xi) SEQUENCE DESCRIPTION: SEQ ID NO: 10:

```
Val Ile Gly His Asp Cys Ala His
1               5
```

(2) INFORMATION FOR SEQ ID NO: 11:

(i) SEQUENCE CHARACTERISTICS:
        (A) LENGTH: 8 amino acids
        (B) TYPE: amino acid
        (D) TOPOLOGY: linear (ii) MOLECULE TYPE: Peptide (xi) SEQUENCE DESCRIPTION: SEQ ID NO: 11:

```
Val Val Gly His Asp Cys Gly His
1               5
```

(2) INFORMATION FOR SEQ ID NO: 12:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 12:

```
His Asn Ala His His
1               5
```

(2) INFORMATION FOR SEQ ID NO: 13:

(i) SEQUENCE CHARACTERISTICS:
        (A) LENGTH: 6 amino acids
        (B) TYPE: amino acid
        (D) TOPOLOGY: linear (ii) MOLECULE TYPE: DNA (peptide)

(xi) SEQUENCE DESCRIPTION: SEQ ID NO: 13:

```
His Asn Tyr Leu His His
1               5
```

(2) INFORMATION FOR SEQ ID NO: 14:

(i) SEQUENCE CHARACTERISTICS:
    (A) LENGTH: 5 amino acids
    (B) TYPE: amino acid
    (D) TOPOLOGY: linear (ii) MOLECULE TYPE: Peptide (xi) SEQUENCE DESCRIPTION: SEQ ID NO: 14:

His Arg Thr His His
1               5

(2) INFORMATION FOR SEQ ID NO: 15:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 15:

His Arg Arg His His
1               5

(2) INFORMATION FOR SEQ ID NO: 16:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 16:

His Asp Arg His His
1               5

(2) INFORMATION FOR SEQ ID NO: 17:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 17:

His Asp Gln His His
1               5

(2) INFORMATION FOR SEQ ID NO: 18:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 18:

His Asp His His His
1               5

(2) INFORMATION FOR SEQ ID NO: 19:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 19:

His Asn His His His
1               5

(2) INFORMATION FOR SEQ ID NO: 20:

(i) SEQUENCE CHARACTERISTICS:
            (A) LENGTH: 6 amino acids
            (B) TYPE: amino acid
            (D) TOPOLOGY: linear (ii) MOLECULE TYPE: Peptide (xi) SEQUENCE DESCRIPTION: SEQ ID NO: 20:

Phe Gln Ile Glu His His
1               5

(2) INFORMATION FOR SEQ ID NO: 21:

(i) SEQUENCE CHARACTERISTICS:
            (A) LENGTH: 6 amino acids
            (B) TYPE: amino acid
            (D) TOPOLOGY: linear (ii) MOLECULE TYPE: Peptide (xi) SEQUENCE DESCRIPTION: SEQ ID NO: 21:

His Gln Val Thr His His
1               5

(2) INFORMATION FOR SEQ ID NO: 22:

(i) SEQUENCE CHARACTERISTICS:
            (A) LENGTH: 5 amino acids
            (B) TYPE: amino acid
            (D) TOPOLOGY: linear (ii) MOLECULE TYPE: Peptide (xi) SEQUENCE DESCRIPTION: SEQ ID NO: 22:

His Val Ile His His
1               5

(2) INFORMATION FOR SEQ ID NO: 23:

(i) SEQUENCE CHARACTERISTICS:
            (A) LENGTH: 5 amino acids
            (B) TYPE: amino acid
            (D) TOPOLOGY: linear (ii) MOLECULE TYPE: Peptide (xi) SEQUENCE DESCRIPTION: SEQ ID NO: 23:

His Val Ala His His
1               5

(2) INFORMATION FOR SEQ ID NO: 24:

(i) SEQUENCE CHARACTERISTICS:
            (A) LENGTH: 5 amino acids
            (B) TYPE: amino acid
            (D) TOPOLOGY: linear (ii) MOLECULE TYPE: Peptide (xi) SEQUENCE DESCRIPTION: SEQ ID NO: 24:

-continued

```
His Ile Pro His His
1               5
```

(2) INFORMATION FOR SEQ ID NO: 25:

(i) SEQUENCE CHARACTERISTICS:
        (A) LENGTH: 5 amino acids
        (B) TYPE: amino acid
        (D) TOPOLOGY: linear (ii) MOLECULE TYPE: Peptide (xi) SEQUENCE DESCRIPTION: SEQ ID NO: 25:

```
His Val Pro His His
1               5
```

(2) INFORMATION FOR SEQ ID NO: 26:

(i) SEQUENCE CHARACTERISTICS:
        (A) LENGTH: 1702 base pairs
        (B) TYPE: nucleic acid
        (C) STRANDEDNESS: both
        (D) TOPOLOGY: linear (ii) MOLECULE TYPE: DNA (genomic)

(ix) FEATURE:
        (A) NAME/KEY: CDS
        (B) LOCATION: 48..1406

(ix) FEATURE:
        (A) NAME/KEY: CDS
        (B) LOCATION: 48..1406

(xi) SEQUENCE DESCRIPTION: SEQ ID NO: 26:

```
CCCCAAAAAT TTTCATTGTT CTCCATCTGG ACCACAGCAT CCACACA ATG GAG GGC        56
                                                    Met Glu Gly
                                                      1

GAA GCT AAG AAG TAT ATC ACG GCG GAG GAC CTC CGC CGC CAC AAC AAG       104
Glu Ala Lys Lys Tyr Ile Thr Ala Glu Asp Leu Arg Arg His Asn Lys
      5               10                  15

TCC GGC GAT CTC TGG ATC TCC ATC CAG GGC AAG GTC TAC GAC TGC TCT       152
Ser Gly Asp Leu Trp Ile Ser Ile Gln Gly Lys Val Tyr Asp Cys Ser
 20              25                  30                  35

CGG TGG GCG GCG GAG CAC CCC GGC GGC GAG GTC CCG CTC CTC AGT CTG       200
Arg Trp Ala Ala Glu His Pro Gly Gly Glu Val Pro Leu Leu Ser Leu
                 40                  45                  50

GCC GGC CAG GAC GTC ACC GAC GCC TTC ATT GCG TAC CAC CCG GGC ACG       248
Ala Gly Gln Asp Val Thr Asp Ala Phe Ile Ala Tyr His Pro Gly Thr
             55                  60                  65

GCG TGG CGG CAT CTG GAT CCG CTC TTC ACC GGC TAC TAC TAC CTC AAG       296
Ala Trp Arg His Leu Asp Pro Leu Phe Thr Gly Tyr Tyr Tyr Leu Lys
         70                  75                  80

GAC TTC GAA GTG TCG GAG ATC TCC AAG GAC TAC CGG AGG CTT TTG AAC       344
Asp Phe Glu Val Ser Glu Ile Ser Lys Asp Tyr Arg Arg Leu Leu Asn
     85                  90                  95

GAG ATG TCG CGG TCC GGG ATC TTC GAG AAG AAG GGC CAC CAC ATC ATG       392
Glu Met Ser Arg Ser Gly Ile Phe Glu Lys Lys Gly His His Ile Met
100                 105                 110                 115

TGG ACG TTC GTC GGC GTT GCG GTC ATG ATG GCG GCA ATC GTC TAC GGC       440
Trp Thr Phe Val Gly Val Ala Val Met Met Ala Ala Ile Val Tyr Gly
                120                 125                 130

GTG CTG GCG TCG GAG TCC GTC GGA GTT CAC ATG CTC TGC GGC GCA CTG       488
Val Leu Ala Ser Glu Ser Val Gly Val His Met Leu Cys Gly Ala Leu
            135                 140                 145
```

-continued

```
CTG GGC TTG CTG TGG ATC CAA GCC GCG TAT GTG GGC CAT GAC TCC GGC          536
Leu Gly Leu Leu Trp Ile Gln Ala Ala Tyr Val Gly His Asp Ser Gly
            150                 155                 160

CAT TAC CAG GTG ATG CCA ACC CGT GGA TAC AAC AGA ATC ACG CAA CTC          584
His Tyr Gln Val Met Pro Thr Arg Gly Tyr Asn Arg Ile Thr Gln Leu
        165                 170                 175

ATA GCA GGC AAC ATC CTA ACC GGA ATC AGC ATC GCG TGG TGG AAG TGG          632
Ile Ala Gly Asn Ile Leu Thr Gly Ile Ser Ile Ala Trp Trp Lys Trp
180                 185                 190                 195

ACC CAC AAC GCC CAC CAC CTC GCC TGC AAC AGC CTC GAC TAC GAC CCC          680
Thr His Asn Ala His His Leu Ala Cys Asn Ser Leu Asp Tyr Asp Pro
                200                 205                 210

GAC CTC CAG CAC ATC CCC GTA TTC GCC GTC TCC ACC CGA CTC TTC AAC          728
Asp Leu Gln His Ile Pro Val Phe Ala Val Ser Thr Arg Leu Phe Asn
            215                 220                 225

TCC ATC ACC TCG GTC TTC TAT GGC CGA GTC CTG AAA TTC GAC GAA GTG          776
Ser Ile Thr Ser Val Phe Tyr Gly Arg Val Leu Lys Phe Asp Glu Val
        230                 235                 240

GCA CGG TTC CTA GTC AGC TAC CAG CAC TGG ACC TAC TAC CCG GTC ATG          824
Ala Arg Phe Leu Val Ser Tyr Gln His Trp Thr Tyr Tyr Pro Val Met
245                 250                 255

ATC TTC GGC CGA GTC AAC CTC TTC ATC CAG ACC TTT TTA TTG CTC CTC          872
Ile Phe Gly Arg Val Asn Leu Phe Ile Gln Thr Phe Leu Leu Leu Leu
260                 265                 270                 275

ACC AGG CGC GAC GTC CCT GAC CGC GCT CTA AAC TTA ATG GGT ATC GCG          920
Thr Arg Arg Asp Val Pro Asp Arg Ala Leu Asn Leu Met Gly Ile Ala
                280                 285                 290

GTT TTC TGG ACG TGG TTC CCG CTC TTC GTA TCT TGT CTC CCG AAC TGG          968
Val Phe Trp Thr Trp Phe Pro Leu Phe Val Ser Cys Leu Pro Asn Trp
            295                 300                 305

CCT GAA CGG TTC GGG TTC GTC CTC ATC AGC TTT GCG GTC ACG GCG ATC         1016
Pro Glu Arg Phe Gly Phe Val Leu Ile Ser Phe Ala Val Thr Ala Ile
        310                 315                 320

CAG CAC GTC CAG TTC ACG CTC AAC CAC TTC TCC GGC GAC ACA TAC GTG         1064
Gln His Val Gln Phe Thr Leu Asn His Phe Ser Gly Asp Thr Tyr Val
325                 330                 335

GGC CCC CCC AAG GGC GAC AAC TGG TTC GAG AAG CAG ACG AAA GGG ACG         1112
Gly Pro Pro Lys Gly Asp Asn Trp Phe Glu Lys Gln Thr Lys Gly Thr
340                 345                 350                 355

ATC GAT ATC ACG TGC CCA CCG TGG ATG GAC TGG TTC TTT GGT GGG CTG         1160
Ile Asp Ile Thr Cys Pro Pro Trp Met Asp Trp Phe Phe Gly Gly Leu
                360                 365                 370

CAG TTC CAG TTG GAG CAC CAC TTG TTC CCT AGG CTG CCG CGT GGG CAG         1208
Gln Phe Gln Leu Glu His His Leu Phe Pro Arg Leu Pro Arg Gly Gln
            375                 380                 385

CTT AGG AAG ATT GCG CCC TTG GCT CGG GAC TTG TGT AAG AAG CAC GGG         1256
Leu Arg Lys Ile Ala Pro Leu Ala Arg Asp Leu Cys Lys Lys His Gly
        390                 395                 400

ATG CCG TAT AGG AGC TTC GGG TTT TGG GAC GAC GCT AAT GTC AGG ACA         1304
Met Pro Tyr Arg Ser Phe Gly Phe Trp Asp Asp Ala Asn Val Arg Thr
405                 410                 415

ATT CGG ACG CTG AGG GAT GCG GCG GTT CAG GCG CGT GAC CTT AAT TCG         1352
Ile Arg Thr Leu Arg Asp Ala Ala Val Gln Ala Arg Asp Leu Asn Ser
                420                 425                 430                 435

GCC CCG TGC CCT AAG AAA CTT GGG TAT GGG GAA GCT TAT AAC ACC CAT         1400
Ala Pro Cys Pro Lys Lys Leu Gly Tyr Gly Glu Ala Tyr Asn Thr His
            440                 445                 450

GGT TGA TTGTGGTTTT GTGTTGTGGG TTGGAGGATC TTCTTATTAT TGATTTATGT         1456
Gly  *
```

```
CCACAATATT GAACTGAATA ACCATGGAAG GCACTACGTT CAGCTTAACT TTGCTTAACT    1516

TTGCTAGCTG GTTGCGTTCC CTTGTTGGGG GCAAAGTGCA GTATTTATTT TCTTATCCCA    1576

TGTACTTTTT GATTATTGTT CTTATTCGTA TCATAAATAA TTTATTATTG ATTAATTTTT    1636

GTTGTAGTTG GGTGTCTATA GCAAGTTTAT AATACTGAGA TATATTTTTT TGGTAAAAAA    1696

AAAAAA                                                                 1702
```

(2) INFORMATION FOR SEQ ID NO: 27:

(i) SEQUENCE CHARACTERISTICS:
        (A) LENGTH: 452 amino acids
        (B) TYPE: amino acid
        (D) TOPOLOGY: linear (ii) MOLECULE TYPE: protein (xi) SEQUENCE DESCRIPTION: SEQ ID NO: 27:

```
Met Glu Gly Glu Ala Lys Lys Tyr Ile Thr Ala Glu Asp Leu Arg Arg
 1               5                  10                  15

His Asn Lys Ser Gly Asp Leu Trp Ile Ser Ile Gln Gly Lys Val Tyr
            20                  25                  30

Asp Cys Ser Arg Trp Ala Ala Glu His Pro Gly Gly Glu Val Pro Leu
        35                  40                  45

Leu Ser Leu Ala Gly Gln Asp Val Thr Asp Ala Phe Ile Ala Tyr His
    50                  55                  60

Pro Gly Thr Ala Trp Arg His Leu Asp Pro Leu Phe Thr Gly Tyr Tyr
65                  70                  75                  80

Tyr Leu Lys Asp Phe Glu Val Ser Glu Ile Ser Lys Asp Tyr Arg Arg
                85                  90                  95

Leu Leu Asn Glu Met Ser Arg Ser Gly Ile Phe Glu Lys Lys Gly His
            100                 105                 110

His Ile Met Trp Thr Phe Val Gly Val Ala Val Met Ala Ala Ile
        115                 120                 125

Val Tyr Gly Val Leu Ala Ser Glu Ser Val Gly Val His Met Leu Cys
    130                 135                 140

Gly Ala Leu Leu Gly Leu Leu Trp Ile Gln Ala Ala Tyr Val Gly His
145                 150                 155                 160

Asp Ser Gly His Tyr Gln Val Met Pro Thr Arg Gly Tyr Asn Arg Ile
                165                 170                 175

Thr Gln Leu Ile Ala Gly Asn Ile Leu Thr Gly Ile Ser Ile Ala Trp
            180                 185                 190

Trp Lys Trp Thr His Asn Ala His His Leu Ala Cys Asn Ser Leu Asp
        195                 200                 205

Tyr Asp Pro Asp Leu Gln His Ile Pro Val Phe Ala Val Ser Thr Arg
    210                 215                 220

Leu Phe Asn Ser Ile Thr Ser Val Phe Tyr Gly Arg Val Leu Lys Phe
225                 230                 235                 240

Asp Glu Val Ala Arg Phe Leu Val Ser Tyr Gln His Trp Thr Tyr Tyr
                245                 250                 255

Pro Val Met Ile Phe Gly Arg Val Asn Leu Phe Ile Gln Thr Phe Leu
            260                 265                 270

Leu Leu Leu Thr Arg Arg Asp Val Pro Asp Arg Ala Leu Asn Leu Met
        275                 280                 285

Gly Ile Ala Val Phe Trp Thr Trp Phe Pro Leu Phe Val Ser Cys Leu
    290                 295                 300
```

-continued

```
Pro Asn Trp Pro Glu Arg Phe Gly Phe Val Leu Ile Ser Phe Ala Val
305                 310                 315                 320

Thr Ala Ile Gln His Val Gln Phe Thr Leu Asn His Phe Ser Gly Asp
                325                 330                 335

Thr Tyr Val Gly Pro Pro Lys Gly Asp Asn Trp Phe Glu Lys Gln Thr
            340                 345                 350

Lys Gly Thr Ile Asp Ile Thr Cys Pro Pro Trp Met Asp Trp Phe Phe
        355                 360                 365

Gly Gly Leu Gln Phe Gln Leu Glu His His Leu Phe Pro Arg Leu Pro
    370                 375                 380

Arg Gly Gln Leu Arg Lys Ile Ala Pro Leu Ala Arg Asp Leu Cys Lys
385                 390                 395                 400

Lys His Gly Met Pro Tyr Arg Ser Phe Gly Phe Trp Asp Asp Ala Asn
                405                 410                 415

Val Arg Thr Ile Arg Thr Leu Arg Asp Ala Ala Val Gln Ala Arg Asp
                420                 425                 430

Leu Asn Ser Ala Pro Cys Pro Lys Lys Leu Gly Tyr Gly Glu Ala Tyr
            435                 440                 445

Asn Thr His Gly
    450
```

What is claimed:

1. A method of inducing production of octadecatetraeonic acid in a plant, which comprises transforming said plant with a nucleotide sequence encoding an evening primrose Δ6-desaturase.

2. The method of claim 1, wherein said nucleotide sequence comprises at least one of the nucleotide sequence of SEQ ID NO: 26 or nucleotides 49 to 1401 of SEQ ID NO: 26.

3. The method of claim 1, wherein said nucleotide sequence encodes SEQ ID NO: 27.

4. A method of inducing production of octadecatetraeonic acid in a plant, which comprises transforming said plant with an expression vector, wherein said vector comprises a nucleotide sequence encoding an evening primrose Δ6-desaturase.

5. The method of claim 4, wherein said nucleotide sequence comprises at least one of the nucleotide sequence of SEQ ID NO: 26 or nucleotides 49 to 1401 of SEQ ID NO: 26.

6. The method of claim 4, wherein said nucleotide sequence encodes SEQ ID NO: 27.

7. A method of inducing production of octadecatetraeonic acid in a plant, which comprises transforming said plant with an expression vector, wherein said vector comprises a promoter and a nucleotide sequence encoding an evening primrose Δ6-desaturase, and wherein said promoter is operably linked to said nucleotide sequence to effect expression of said evening primrose Δ6-desaturase.

8. The method of claim 7, wherein said nucleotide sequence comprises at least one of the nucleotide sequence of SEQ ID NO: 26 or nucleotides 49 to 1401 of SEQ ID NO: 26.

9. The method of claim 7, wherein said nucleotide sequence encodes SEQ ID NO: 27.

10. A method of inducing production of octadecatetraeonic acid in a plant, which comprises transforming said plant with an expression vector, wherein said vector comprises a promoter, a termination signal and a nucleotide sequence encoding an evening primrose Δ6-desaturase, and wherein said promoter and said termination signal are operably linked to said nucleotide sequence to effect expression of said evening primrose Δ6-desaturase.

11. The method of claim 10, wherein said nucleotide sequence comprises at least one of the nucleotide sequence of SEQ ID NO: 26 or nucleotides 49 to 1401 of SEQ ID NO: 26.

12. The method of claim 10, wherein said nucleotide sequence encodes SEQ ID NO: 27.

13. The method of any one of claims 7-12, wherein said promoter is selected from a Δ6-desaturase promoter, an *Anabaena* carboxylase promoter, a helianthinin promoter, a glycinin in promoter, a napin promoter, the 35S promoter from CaMV, a helianthinin tissue-specific promoter, an oleosin seed-specific promoter, or an albumin seed-specific promoter.

14. The method of any one of claims 1-12, wherein said plant is a sunflower, soybean, maize, tobacco, peanut, carrot or oil seed rape plant.

15. The method of claim 13, wherein said plant is a sunflower, soybean, maize, tobacco, peanut, carrot or oil seed rape plant.

16. A method of inducing production of octadecatetraeonic acid in a plant, which comprises transforming said plant with a nucleotide sequence, wherein said nucleotide sequence encodes a plant Δ6-desaturase and hybridizes under stringency conditions to the complement of a polynucleotide sequence coding for an evening primrose Δ6-desaturase, wherein said polynucleotide sequence comprises SEQ ID NO: 26 or nucleotides 49 to 1401 of SEQ ID NO: 26, and wherein said stringency conditions comprise hybridization to filter-bound DNA in 6×SSC, 1× Denharts solution, 0.05% sodium pyrophosphate, 100 μg/ml denatured salmon sperm DNA at 60° C., and washing in 4×, 2×, and 1×SET at 60° C.

17. A method of inducing production of octadecatetraenoic acid in a plant, which comprises transforming said plant with a nucleotide sequence, wherein said nucleotide sequence encodes a plant Δ6-desaturase and hybridizes under stringency conditions to the complement of a polynucleotide sequence molecule coding for a plant delta-6 desaturase which comprises
SEQ ID NO: 6,
SEQ ID NO: 12, and
SEQ ID NO: 20,
and wherein said stringency conditions comprise hybridization to filter-bound DNA in 6×SSC, 1× Denharts solution, 0.05% sodium pyrophosphate, 100 g/ml denatured salmon sperm DNA at 60° C., and washing in 4×, 2×, and 1×SET at 60° C.

18. A method of inducing production of octadecatetraenoic acid in a plant, which comprises transforming said plant with a nucleotide sequence, wherein said nucleotide sequence encodes a plant Δ6-desaturase and hybridizes under stringency conditions to the complement of a polynucleotide sequence molecule coding for a plant delta-6 desaturase which comprises amino acids 159-164, 197-201 and 373-378 of SEQ ID NO: 27, and wherein said stringency conditions comprise hybridization to filter-bound DNA in 6×SSC, 1× Denharts solution, 0.05% sodium pyrophosphate, 100 μg/ml denatured salmon sperm DNA at 60° C., and washing in 4×, 2×, and 1×SET at 60° C.

19. The method according to any one of claims 16-18, wherein said nucleotide sequence that encodes said plant Δ6-desaturase is placed in an expression vector which comprises a promoter, and wherein said promoter is operably linked to said nucleotide sequence to effect expression of said plant Δ6-desaturase.

20. The method of claim 19, wherein said promoter is selected from a Δ6-desaturase promoter, an *Anabaena* carboxylase promoter, a helianthinin promoter, a glycinin in promoter, a napin promoter, the 35S promoter from CaMV, a helianthinin tissue-specific promoter, an oleosm seed-specific promoter, or an albumin seed-specific promoter.

21. The method of any one of claims 16-18, wherein said plant is a sunflower, soybean, maize, tobacco, peanut, carrot or oil seed rape plant.

* * * * *

UNITED STATES PATENT AND TRADEMARK OFFICE
CERTIFICATE OF CORRECTION

PATENT NO. : 7,282,623 B2  
APPLICATION NO. : 10/702777  
DATED : October 6, 2007  
INVENTOR(S) : Terry L. Thomas It is certified that error appears in the above-identified patent and that said Letters Patent is hereby corrected as shown below:

Title Page, Item (60) should read
--(60) Division of U.S. Ser. No. 09/685,775 filed Oct. 10, 2000, U.S. Pat. No. 6,683,232, which is a divisional of application No. 08/934,254, filed Sep. 19, 1997, U.S. Pat. No. 6,355,861 which is a continuation-in-part of 08/789,936 filed Jan. 28, 1997, U.S. Pat No. 5,789,220 which is a continuation of 08/366,779 filed Dec. 30, 1994, U.S. Pat. No. 5,614,393 which is a continuation-in-part of 08/307,382 filed Sep. 14, 1994, U.S. Pat. No. 5,552,306 which is a continuation of 07/959,952 filed Oct. 13, 1992, abandoned, which is a continuation-in-part of 07/817,919 filed Jan. 8, 1992, abandoned, which is a continuation-in-part of 07/774,475 filed Oct. 10, 1991, abandoned.--

Signed and Sealed this

Twenty-eighth Day of September, 2010

David J. Kappos
*Director of the United States Patent and Trademark Office*